US006534275B1

(12) United States Patent
Stuart et al.

(10) Patent No.: US 6,534,275 B1
(45) Date of Patent: *Mar. 18, 2003

(54) CELLUBREVIN HOMOLOGS

(75) Inventors: Susan G. Stuart, Montara, CA (US); Phillip R. Hawkins, Mountain View, CA (US); Jeffrey J. Seilhamer, Los Altos Hills, CA (US); Lynn E. Murry, Portola Valley, CA (US)

(73) Assignee: Incyte Genomics, Corp., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/483,665

(22) Filed: Jan. 14, 2000

Related U.S. Application Data

(60) Division of application No. 08/621,018, filed on Mar. 22, 1996, now Pat. No. 6,060,239, which is a continuation-in-part of application No. 08/409,373, filed on Mar. 23, 1995, now Pat. No. 5,650,280.

(51) Int. Cl.[7] ........................ G01N 33/53; A61K 38/00; C07K 14/00; C07K 1/00
(52) U.S. Cl. ........................ 435/7.1; 530/700; 530/350
(58) Field of Search ................................ 530/350, 300; 435/7.1

(56) References Cited

U.S. PATENT DOCUMENTS 5,650,280 A  7/1997  Stuart et al. .................... 435/6

OTHER PUBLICATIONS

McMahon et al., "Cellubrevin is a ubiquitous tetanus–toxin substrate homologous to a putative synaptic vesicle fusion protein", *Nature*, 364:346–349 (1993).
Arora, Naveen, "Cytotoxic Effects of a Chimeric Protein Consisting of Tetanus Toxin Light Chain and Anthrax Toxin Lethal Factor in Non–neuronal Cells", *J. Biol. Chem.*, 269:26165–26171 (1994).
Bark et al., "Regulated vesicular fusion in neurons: Snapping together the details", *Proc. Natl. Acad. Sci. USA*, 91:4621–4624 (1994).
Link et al., "Cleavage of Cellubrevin by Tetanus Toxin Does Not Affect Fusion of Early Endosomes", *J. Biol. Chem.*, 268–18423–18426 (1993).
Maniatis et al., *Molecular Cloning, A Laboratory Manual*, Cold Spring Harbor Press, Plainview, NY (1989).
Ausubel FM et al., *Current Protocols in Molecular Biology*, John Wiley & Sons, New York, NY (1989).
Hohlfeld P. et al., "Prenatal diagnosis of congenital toxoplasmosis with a polymerase chain reaction test on amniotic fluid", *New England Journal of Medicine*, 331:695–699 (1994).
Mulder J. et al., "Rapid and simple PCR assay for quantitation of human immunodeficiency virus type 1 RNA in plasma:Application to acute retroviral infection", *J. Clin. Microbiol.* 31:292–300 (1994).
Ralston et al., "Expression of the Synaptic Vesicle Proteins VAMPs/Synaptobrevins 1 and 2 in Non–neural Tissues", *J. Biol. Chem.*, 269:15403–15406 (1994).
Archer et al., "Structures and chromosomal localizations of two human genes encoding synaptobrevins 1 and 2", *J. Biol. Chem.*, vol. 265, No. 28, pp 17267–17273, (1990).
McMahon et al., "Cellubrevin: a substrate for tetanus toxin found on a constitutive vesicle recycling pathway is a homologue of synaptobrevin", Soc. Neurosci. Abst., vol. 19, No. 1–3, p.900, (1993).
Sengupta et al., "Identification of novel isoforms of cellubrevin in rat pancreatic acinar cells", *Mol. Biol. Cell.*, vol. 5, p.116A (1994).
Galli et al., "Cellubrevin is not restricted to transferrin receptor–containing vesicles in PC12 cells and colocalizes with synaptobrevin I and II", *Mol. Biol. Cell.*, vol. 5, p. 325A (1994).
Galli et al., "Tetanus toxin–mediated cleavage of cellubrevin impairs exocytosis of transferrin receptor–contianing vesicles in CHO cells", *J. Cell. Biol.*, vol. 125, No. 5, pp 1015–1024 (1994).
Jacobsson et al., "Identification of synaptic proteins and their isoform mRNAs in compartments of pancreatic endocrine cells", *Proc. Natl Acad. Sci.*, 91:12487–12491 (1994).
Sudhof et al., "A synaptic vesicle membrane protein is conserved from mammals to Drosophila", *Neuron*, 2:1475–1481 (1989).
Baumert et al., "Synaptobrevin: an integral membrane protein of 18 000 daltons present in small synaptic vesicles of rat brain", *Embo. J.* 8(2): 379–384 (1989).
Richter, K. et al., "Gene expression in the embroyonic nervous system of Xenopus laevis", *Proc. Natl. Acad. Sci. USA* 85: 8086–90 (1988) (Accession GI 388483).

*Primary Examiner*—W. Gary Jones
*Assistant Examiner*—Jehanne Souaya
(74) *Attorney, Agent, or Firm*—Incyte Genomics, Corp.

(57) ABSTRACT

The present invention provides nucleotide and amino acid sequences that identify and encode novel cellubrevins (cb). The present invention also provides for antisense molecules to the nucleotide sequences which encode cbs, expression vectors for the production of purified CBs, antibodies capable of binding specifically to CBs, hybridization probes or oligonucleotides for the detecting the induction of CB encoding nucleotide sequences, genetically engineered host cells for the expression of CBs, diagnostic tests for activated, inflamed or diseased cells and/or tissues based on CB-encoding nucleic acid molecules and antibodies capable of binding specifically to CBs.

16 Claims, 5 Drawing Sheets

```
                 9                  18                  27                  36                  45                  54
5' ATG GAG GAA GCC AGT GAA GGT GGA GGA AAT GAT CGT TTG CGG AAC CTG CAA AGT
    M   E   E   A   S   E   G   G   G   N   D   R   L   R   N   L   Q   S 63                  72                  81                  90                  99                 108
    GAG GTG GAG GGA GTT AAG AAT ATT ATG ACC CAG AAT GTG GAG CGG ATC CTG GCC
     E   V   E   G   V   K   N   I   M   T   Q   N   V   E   R   I   L   A 117                 126                 135                 144                 153                 162
    CGG GGG GAA AAC TTG GAA CAT CTC CGC AAC AAG ACA GAG GAT CTG GAA GCC ACA
     R   G   E   N   L   E   H   L   R   N   K   T   E   D   L   E   A   T 171                 180                 189                 198                 207                 216
    TCT GAG CAC TTC AAG ACG ACA TCG CAG AAG GTG GCT CGA AAA TTC TGG TGG AAG
     S   E   H   F   K   T   T   S   Q   K   V   A   R   K   F   W   W   K 225                 234                 243                 252                 261                 270
    AAC GTG AAG ATG ATT GTC CTT ATC TGC GTG ATT GTT TTT ATC ATC ATC CTC TTC
     N   V   K   M   I   V   L   I   C   V   I   V   F   I   I   I   L   F 279                 288                 297                 306
    ATT TGT GCT CTT TGC CAC TGG TGC CTT CTT CTT AAG TAA  3'
     I   C   A   L   C   H   W   C   L   L   L   K   *
```

FIGURE 1

```
                 9              18             27             36             45             54
5' ATG GCA GGA ATA GAG TTG GAG CGG TGC CAG CAG CAG GCG AAT GAG GTG ACG GAA
    M   A   G   I   E   L   E   R   C   Q   Q   Q   A   N   E   V   T   E 63             72             81             90             99            108
   ATT ATG CGT AAC AAC TTC GGC AAG GTC CTG GAG CGT GGT GTG AAG CTG GCC GAA
    I   M   R   N   N   F   G   K   V   L   E   R   G   V   K   L   A   E 117            126            135            144            153            162
   CTG CAG CAG CGT TCA GAC CAA CTC CTG GAT ATG AGC TCA ACC TTC AAC AAG ACT
    L   Q   Q   R   S   D   Q   L   L   D   M   S   S   T   F   N   K   T 171            180            189            198            207            216
   ACA CAG AAC CTG GCC CAG AAG AAG TGC TGG GAG AAC ATC CGT TAC CGG ATC TGC
    T   Q   N   L   A   Q   K   K   C   W   E   N   I   R   Y   R   I   C 225            234            243            252            261            270
   GTG GGG CTG GTG GTG GTT GGT GTC CTG CTC ATC ATC CTG ATT GTG CTG CTG GTC
    V   G   L   V   V   V   G   V   L   L   I   I   L   I   V   L   L   V 279            288            297            306            315            324
   GTC TTT CTC CCT CAG AGC AGT GAC AGC AGT AGT GCC CCA CGG ACC CAG GAT GCA
    V   F   L   P   Q   S   S   D   S   S   S   A   P   R   T   Q   D   A 333            342            351
   GGC ATT GCC TCA GGG CCT GGG AAC TGA  3'
    G   I   A   S   G   P   G   N   *
```

FIGURE 2

```
                9                18               27               36               45               54
5' ATG TCT ACA GGT CCA ACT GCT GCC ACT GGC AGT AAT CGA AGA CTT CAG CAG ACA
   M   S   T   G   P   T   A   A   T   G   S   N   R   R   L   Q   Q   T 63               72               81               90               99              108
   CAA AAT CAA GTA GAT GAG GTG GTG GAC ATA ATG CGA GTT AAC GTG GAC AAG GTT
   Q   N   Q   V   D   E   V   V   D   I   M   R   V   N   V   D   K   V 117              126              135              144              153              162
   CTG GAA AGA GAC CAG AAG CTC TCT GAG TTA GAC GAC CGT GCA GAC GCA CTG CAG
   L   E   R   D   Q   K   L   S   E   L   D   D   R   A   D   A   L   Q 171              180              189              198              207              216
   GCA GGC GCT TCT CAA TTT GAA ACG AGC GCA GCC AAG TTG AAG AGG AAA TAT TGG
   A   G   A   S   Q   F   E   T   S   A   A   K   L   K   R   K   Y   W 225              234              243              252              261              270
   TGG AAG AAC TGC AAG ATG TGG GCA ATC GGG ATT ACT GTT CTG GTT ATC TTC ATC
   W   K   N   C   K   M   W   A   I   G   I   T   V   L   V   I   F   I 279              288              297
   ATC ATC ATC ATC GTG TGG GTT GTC TCT TCA TGA   3'
   I   I   I   I   V   W   V   V   S   S   *
```

FIGURE 3

```
              9           18           27           36           45           54
5' ATG CCT CCC AAG TTT AAG CGC CAC CTC AAT GAT GAT GAT GTC ACA GGT TCT GTG
   M   P   P   K   F   K   R   H   L   N   D   D   D   V   T   G   S   V 63          72          81          90          99         108
   AAA AGT GAA AGG AGA AAT CTT TTG GAA GAT GAT TCA GAT GAA GAA GAG GAC TTT
   K   S   E   R   R   N   L   L   E   D   D   S   D   E   E   E   D   F 117         126         135         144         153        162
   TTT CTA AGG GGA CCA TCT GGA CCA AGA TTT GGA CCT AGA AAT GAT AAA ATT AAG
   F   L   R   G   P   S   G   P   R   F   G   P   R   N   D   K   I   K 171         180         189         198         207        216
   CAT GTT CAG AAT CAA GTG GAT GAA GTT ATT GAT GTC ATG CAA GAA AAT ATT ACA
   H   V   Q   N   Q   V   D   E   V   I   D   V   M   Q   E   N   I   T 225         234         243         252         261        270
   AAG GTA ATT GAG AGA GGG GAG AGA CTA GAT GAA CTA CAG GAC AAA TCA GAA AGC
   K   V   I   E   R   G   E   R   L   D   E   L   Q   D   K   S   E   S 279         288         297         306         315        324
   TTA TCG GAT AAT GCA ACA GCT TTT AGC AAC AGA TCC AAA CAA CTT CGA AGG CAA
   L   S   D   N   A   T   A   F   S   N   R   S   K   Q   L   R   R   Q 333         342         351         360         369        378
   ATG TGG TGG CGT GGA TGC AAA ATA AAA GCC ATC ATG GCT TTG GTT GCT GCT ATC
   M   W   W   R   G   C   K   I   K   A   I   M   A   L   V   A   A   I 387         396         405         414         423
   CTT TTG CTA GTG ATT ATC ATT CTT ATA GTC ATG AAA TAC CGT ACT TGA  3'
   L   L   L   V   I   I   I   L   I   V   M   K   Y   R   T   *
```

CELLUBREVIN HOMOLOGS

This application is a divisional application of U.S. application Ser. No. 08/621,018, filed on Mar. 22, 1996 now U.S. Pat. No. 6,060,239, which is a continuation-in-part of U.S. application Ser. No. 08/409,373, filed on Mar. 23, 1995, issued Jul. 22, 1997, as U.S. Pat. No. 5,650,280.

TECHNICAL FIELD

The present invention is in the field of molecular biology; more particularly, the present invention describes the nucleic acid and amino acid sequences of three novel cellubrevin homologs.

BACKGROUND ART

Cellubrevins are homologs of synaptobrevins, synaptic vesicle-associated membrane proteins (VAMPs). Synaptobrevin was first discovered in rat brain (Baumert et al (1989) Embo J 8:379–84) and initially thought to be limited to neuronal cells. Synaptobrevin is an integral membrane protein of 18 kDA (Ralston E et al (1994) J Biol Chem 269:15403–6) involved in the movement of vesicles from the plasmalemma of one cell, across the synapse, to the plasma membrane of the receptive neuron. This regulated vesicle trafficking pathway and the endocytotic process may be blocked by the highly specific action of clostridial neurotoxins which prevents neurotransmitter release by cleaving the synaptobrevin molecule. Synaptobrevins are now known to occur and function in constitutive vesicle trafficking pathways involving the receptor-mediated endocytotic and exocytotic pathways of many non-neuronal cell types.

Cellubrevins are 16 kDa proteins first found and investigated in rat cells and tissues (McMahon HT et al (1993) Nature 364:346–9). In vitro studies of various cellular membranes (Galli et al (1994) J Cell Biol 125:1015–24; Link et al (1993) J Biol Chem 268:18423–6) have shown that VAMPS including the cellubrevins are widely distributed and are important in membrane trafficking. They appear to participate in axon extension via exocytosis during development, in the release of neurotransmitters and modulatory peptides, and in endocytosis. Endocytotic vesicular transport includes such intracellular events as the fusions and fissions of the nuclear membrane, endoplasmic reticulum, Golgi apparatus, and various inclusion bodies such as peroxisomes or lysosomes.

Endocytotic processes appear to be universal in eukaryotic cells as diverse as yeast, *Caenorhabditis elegans*, Drosophila, and humans. The homologous proteins which direct the movement of vesicles within and between the cells of these organisms contain evolutionarily conserved domains. Generally, VAMPs have a three domain organization. The domains include a variable proline-rich, N-terminal sequence of 28 amino acids, a highly conserved central hydrophilic core of 69 amino acids, and a hydrophobic sequence of 23 amino acids presumed to be the membrane anchor.

As mentioned for synaptobrevin above, cellubrevins are sensitive to selective proteolysis by metalloendoproteases such as the zinc endoprotease which comprises the light chain of tetanus toxin. Experiments have shown that endosome fusion may continue even after specific cellubrevin cleavage through temperature- and ATP-dependent docking and fusion processes involving N-ethylmaleimide-sensitive fusion proteins (NSF) and small, soluble attachment proteins (SNAP).

Because tissue distribution and VAMPs are more numerous and widely distributed than initially recognized, research on their differential expression and subcellular localization may turn out to be one of the most fruitful areas for the control or amelioration of diseases and disease symptoms.

Cellubrevins are associated with particular cell types, participate in both intracellular and extracellular pathways, and appear to vary in their abundance and specificity. Elucidation of the interactions of the novel cellubrevins (and associated VAMPs) with docking proteins such as syntaxin and SNAPs of the plasmalemma or the core fusion proteins such as NSF and the synaptotagmins (Bark I C and Wilson M C (1994) Proc Natl Acad Sci 91:4621–4624) provide means for the regulation of vesicle trafficking in normal as well as acute and chronic disease situations.

DISCLOSURE OF THE INVENTION

The subject invention provides nucleotide sequences which uniquely encode novel human cellubrevins. The cDNAs, disclosed herein, are designated: 1) cb-1 (SEQ ID NO:1) which was found within Incyte Clone No. 80184 and encodes a polypeptide designated CB-1 (SEQ ID NO:2); 2) cb-2 (SEQ ID NO:3) which was found within Incyte Clone No. 122826 and encodes a polypeptide designated CB-2 (SEQ ID NO:4), 3) cb-3 (SEQ ID NO:5) which was identified and extended using Incyte Clone No. 311537 and encodes a polypeptide designated CB-3 (SEQ ID NO:6); and 4) cb-4 (SEQ ID NO:7) which was found within Incyte Clone No. 674 719 and encodes a polypeptide designated CB-4 (SEQ ID NO:8).

The invention also comprises using these CBs or their variants to intercede in conditions involving physiologic or pathologic compromise which include the steps of testing a sample or an extract with cb nucleic acids, fragments or oligomers thereof. Aspects of the invention include the antisense of the nucleic acid sequences; cloning or expression vectors containing the nucleic acid sequences; host cells or organisms transformed with these expression vectors; a method for the production and recovery of purified CBs from host cells; and purified proteins which may be used to generate antibodies for diagnosis or therapy of activated or inflamed cells and/or tissues.

BRIEF DESCRIPTION OF DRAWINGS

FIG. 1 shows the nucleotide (SEQ ID NO:1) and amino acid (SEQ ID NO:2) sequences of CB-1 (Incyte Clone 80814).

FIG. 2 shows the nucleotide (SEQ ID NO:3) and amino acid (SEQ ID NO:4) sequences of CB-2 (Incyte Clone 122826).

FIG. 3 shows the nucleotide (SEQ ID NO:5) and amino acid (SEQ ID NO:6) sequences of CB-3 (Incyte Clone 311537).

FIG. 4 shows the nucleotide (SEQ ID NO:7) and amino acid (SEQ ID NO:8) sequences of CB-4 (Incyte Clone 674719).

FIG. 5 shows amino acid alignments among the new cellubrevins and their closest known homologs, rat synaptobrevin (SEQ ID NO:9; GI 388483), bovine synaptobrevin (SEQ ID NO:10; GI 433075), and Xenopus synaptobrevin (SEQ ID NO:11; GI 606978). Alignments shown were produced using the multisequence alignment program of DNASTAR software (DNASTAR Inc, Madison Wis.), and consensus residues are boxed. The plurality of the molecules have the $K_{39}VLER_{42}$ motif, the $W_{76}W_{77}$ motif as described in GI 388483, and all have prominent C terminal isoleucine and valine residues which allow vesicle localization within the membrane

MODES FOR CARRYING OUT THE INVENTION

Three new cellubrevin homologs were discovered among the partial nucleotide sequences in three different Incyte cDNA libraries. Incyte Clone No. 80184 was found among the cDNAs of a rheumatoid synovium library (SYNORAB01); Incyte Clone No. 122826 was found among the cDNAs of a lung library (LUNGNOT01); Incyte Clone No. 311537 was found among the cDNAs of a lung library (LUNGNOT02); and Incyte Clone No. 674719 was found among the cDNAs of a cerebellum library (CRBLNOT02)

As used herein, CB (upper case), refers to cellubrevin polypeptides, naturally occurring CBs and active fragments thereof, which are encoded by mRNAs transcribed from cDNAs or cb (lower case).

"Active" refers to those forms of CB which retain the biologic and/or immunologic activities of any naturally occurring CB.

"Naturally occurring CB" refers to CBs produced by cells that have not been genetically engineered and specifically contemplates various CBs arising from post-translational modifications of the polypeptide including, but not limited to, acetylation, carboxylation, glycosylation, phosphorylation, lipidation and acylation.

"Derivative" refers to CBs chemically modified by such techniques as ubiquitination, labeling (e.g., with radionuclides or various enzymes), pegylation (derivatization with polyethylene glycol), and insertion or substitution by chemical synthesis of amino acids such as ornithine, which do not normally occur in human proteins.

"Recombinant variant" refers to any polypeptide differing from naturally occurring CBs by amino acid insertions, deletions, and substitutions, created using recombinant DNA techniques. Guidance in determining which amino acid residues may be replaced, added or deleted without abolishing activities of interest, such as cellular trafficking, may be found by comparing the sequence of the particular CB with that of homologous peptides and minimizing the number of amino acid sequence, changes made in regions of high homology.

Preferably, amino acid "substitutions" are the result of replacing one amino acid with another amino acid having similar structural and/or chemical properties, such as the replacement of a leucine with an isoleucine or valine, an aspartate with a glutamate, or a threonine with a serine, i.e., conservative amino acid replacements. "Insertions" or "deletions" are typically in the range of about 1 to 5 amino acids. The variation allowed may be experimentally determined by systematically making insertions, deletions, or substitutions of amino acids in a CB molecule using recombinant DNA techniques and assaying the resulting recombinant variants for activity.

Where desired, an expression vector may be designed to contain a "signal or leader sequence" which will direct the CB polypeptide through the membrane of a cell. Such a sequence may be naturally present on the polypeptides of the present invention or provided from heterologous protein sources by recombinant DNA techniques.

A polypeptide "fragment," "portion," or "segment" is a stretch of amino acid residues of at least about 5 amino acids, often at least about 7 amino acids, typically at least about 9 to 13 amino acids, and, in various embodiments, at least about 17 or more amino acids. To be active, any CB polypeptide must have sufficient length to display biologic and/or immunologic activity.

An "oligonucleotide" or polynucleotide "fragment", "portion," or "segment" is a stretch of cb nucleotide residues which is long enough to use in polymerase chain reaction (PCR) or various hybridization procedures to identify or amplify identical or related parts of mRNA or DNA molecules.

The present invention comprises purified CB polypeptide from natural or recombinant sources, as well as from chemical synthesis. The instant invention also relates to cells transformed with recombinant nucleic acid molecules encoding CB. Various methods for the isolation of CB polypeptide may be accomplished by procedures well known in the art. For example, such a polypeptide may be purified by immunoaffinity chromatography by employing the antibodies provided by the present invention. Various other methods of protein purification well known in the art include those described in Deutscher M (1990) Methods in Enzymology, Vol 182, Academic Press, San Diego; and in Scopes R (1982) Protein Purification: Principles and Practice, Springer-Verlag, New York N.Y., both incorporated herein by reference.

"Recombinant" may also refer to a polynucleotide which encodes CB and is prepared using recombinant DNA techniques. The DNA which encodes CB may also include allelic or recombinant variants and mutants thereof.

"Oligonucleotides" or "nucleic acid probes" are prepared based on the cDNA sequence provided in the present invention which encodes GB. Oligonucteotides comprise portions of the cb DNA sequence having at least about 15 nucleotides and usually at least about 20 nucleotides. Nucleic acid probes comprise portions of the sequence having fewer nucleotides than about 6 kb, usually fewer than about 1 kb. After appropriate testing to eliminate false positives, these probes may be used to determine whether mRNAs encoding CB are present in a cell or tissue or to isolate similar nucleic acid sequences from chromosomal DNA as described by Walsh P S et al (1992 PCR Methods Appl 1:241–250).

Probes may be derived from naturally occurring or recombinant single- or double-stranded nucleic acids or may be chemically synthesized. They may be labeled by nick translation, Klenow fill-in reaction, PCR or other methods well known in the art. Probes of the present invention, their preparation and/or labeling are elaborated in Sambrook J et al (1989) Molecular Cloning: A Laboratory Manual, Cold Spring Harbor Laboratory, NY; or Ausubel F M et al (1989) Current Protocols in Molecular Biology, John Wiley & Sons, New York N.Y., both incorporated herein by reference.

"Activated" cells as used in this application are those which are engaged in extracellular or intracellular membrane trafficking, including the export of neurosecretory or enzymatic molecules as part of a normal or disease process.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the cb sequence may be reflected in the CB polypeptide or domains of other peptides added to the CB polypeptide to modify the properties of any part of the polypeptide, to change characteristics such as ligand-binding affinities, interchain affinities, or degradation/turnover rate.

DETAILED DESCRIPTION OF THE INVENTION

The present invention provides nucleotide sequences which uniquely identify novel human cellubrevins. Because CBs are specifically expressed in active, and perhaps protective cells, the nucleic acids (cbs), polypeptide (CBs) and antibodies to CB are useful in investigations of and interventions in physiologic or pathologic processes. Exocytosis governed by CBs may direct membrane trafficking within the cell and affect release of chemokines which are involved in cell migration, proteases which are active in inflammation or other molecules which are specific to the activities of endothelial cells, fibroblasts, or lymphocytes.

The cb-1 of this application (SEQ ID NO:1) was isolated from a rheumatoid synovium library and is most closely related to rat synaptobrevin II (GI 388483; McMahon, H T et al. (1993) Nature 364:346–9). Transcripts (SEQ ID Nos:12–33) exactly matching or overlapping cb-1 sequence were electronically identified from 14 different libraries which reflect cells and tissues affected by disease and/or involved in systemic defense. Transcripts appear in libraries made from eosinophils (EOSIHET02), lymphocytes (TMLR3DT02) and macrophages (MPHGNOT02; MMLR2DT01); two lymphoid tissues, thymus (THYMNOT02) and tonsil (TONSNOT01); tissues where systemic defense routinely occurs, such as lung (LUNGNOT02), small intestine (SINTNOT02), and kidney KIDNNOT02); or disease and inflamed tissues such as the rheumatoid synovia (SYNORAB01, SYNORAT01, and SYNORAT04), the prostate (PROSNOT01) removed from a 78 year old man, and prostate (PROSTUT03) and breast tumors (BRSTTUT01). The cb-1 sequence is useful as a diagnostic for rheumatoid arthritis, breast and prostate tumor and for confirming the activation of the immune system in systemic defense.

The cb-2 of this application (SEQ ID NO:3) was isolated from a lung library (LUNGNOT01) and is most closely related Xenopus synaptobrevin II (GI 606978; Knecht A K (1988) Proc Nat Acad Sci 8086–90). Transcripts (SEQ ID NOs. 34–40) exactly matching or overlapping cb-2 sequence were electronically identified from five different libraries which reflect cells and tissues of ectodermal, neural or tumor origin. The cb-2 transcript appears in libraries made from the non-tumorous lung tissue of a 79 year old man who smoked approximately 100 packs of cigarettes per year and had lung cancer (LUNGNOT01 and LUNGNOT03), heart (LATRNOT01 and LVENNOT02), brain tumor (BRAITUT01), colon from a 40 year old Caucasian male with Crohn's disease (COLNNOT05) and uterus removed from a 34 year old Caucasian female (UTRSNOT02). The cb-2 sequence is useful as a diagnostic for cell proliferation in ectodermal and neural tissues, particularly for Crohn's disease, lung cancer or brain tumors.

The cb-3 of this application (SEQ ID NO:5) was identified among the cDNAs from lung tissue (LUNGNOT02) removed from a 47 yr old Caucasian male who died after a subarachnoid hemorrhage. The sequence was used to produce the full length cDNA which was then determined to be most closely related to bovine synaptobrevin (GI 433075; Sudhof T C et al. (1989) Neuron 2:1475–81). Transcripts (SEQ ID NOs. 41–49) exactly matching or overlapping cb-3 sequence were electronically identified from nine different libraries. The cells and tissues represent essentially four tissue sources which share active endothelial cells and/or function in systemic defense. The cells and tissues are cultured human umbilical vein endothelial cells (HUVENOB01), lung (previously described, LUNGNOT01), heart atria (RATRNOT01 and LATRNOT01), and small intestine (SINTNOT02). The cb-3 sequence is useful as a diagnostic for conditions, particularly infection, inflammation and other stresses affecting the endothelium, particularly the cardiovascular endothelium.

The cb-4 of this application (SEQ. ID NO:7) was isolated from cerebellar tissue (CRBLNOT01) removed from a 69 year old Caucasian male who died of chronic obstructive pulmonary disease. The cb-4 sequence represents a new class of cellubrevin molecules which has not been described previously. It has only limited identity with the other molecules disclosed herein and is not found in any other Incyte libraries. The cb-4 sequence is useful as a diagnostic for conditions which injure the cerebellum such as anoxia; cerebellum degenerative diseases such as multiple sclerosis tuberous sclerosis, and Wilson's disease; infectious diseases caused by viruses, bacteria, fungi or parasites including but not limited to malaria, whooping cough, mumps, encephalitis, polio, syphilis, or tuberculosis; or tumors of the central nervous system such as astrocytomas, medulla blastomas, ependymomas, and hemangeoblastomas which induce expression of the human gene.

With each of the cellubrevins, a diagnostic test for upregulated expression of the particular CB helps in the diagnosis and proper treatment of conditions caused by viral or other infections, traumatic tissue damage, hereditary diseases such as arthritis or asthma, invasive cancers, leukemias and lymphomas; or other physiologic/pathologic problems associated with induced, and otherwise abnormal, membrane trafficking.

The nucleotide sequences encoding the CBs (or their complements) have numerous applications in techniques known to those skilled in the art of molecular biology. These techniques include use as hybridization probes, use as oligomers for PCR, use for chromosome and gene mapping, use in the recombinant production of CBs, and use in generation of anti-sense DNA or RNA, their chemical analogs and the like. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

It will be appreciated by those skilled in the art that as a result of the degeneracy of the genetic code, a multitude of CB-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring CBs, and all such variations are to be considered as being specifically disclosed.

Although nucleotide sequences which encode the CBs and their variants are preferably capable of hybridizing to the nucleotide sequence of the naturally occurring cb under stringent conditions, it may be advantageous to produce nucleotide sequences encoding CBs or their derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding CBs and their derivatives without altering the encoded amino acid sequences include the production of RNA transcripts having more desirable properties, such as a greater half-life, than transcripts produced from the naturally occurring sequence.

The nucleotide sequences encoding CBs may be joined to a variety of other nucleotide sequences by means of well established recombinant DNA techniques (cf Sambrook J et al. (1989) Molecular Cloning: A Laboratory Manual, Cold Spring Harbor Laboratory, NY). Useful nucleotide sequences for joining to cbs include an assortment of cloning vectors, e.g., plasmids, cosmids, lambda phage derivatives, phagemids, and the like, that are well known in the art. Vectors of interest include expression vectors, replication vectors, probe generation vectors, and sequencing vectors. In general, vectors of interest will contain an origin of replication functional in at least one organism, convenient restriction endonuclease sensitive sites, and selectable markers for the host cell.

Another aspect of the subject invention is to provide for cb-specific nucleic acid hybridization probes capable of hybridizing with naturally occurring nucleotide sequences encoding CB. Such probes may also be used for the detection of related cellubrevin encoding sequences and should preferably contain at least 50% of the nucleotides from any of these CB encoding sequences. The hybridization probes of the subject invention may be derived from the nucleotide sequence of the SEQ ID NOs:1, 3, 5, or 7 or from genomic sequence including promoter, enhancer elements and introns of the naturally occurring cbs. Hybridization probes may be labeled by a variety of reporter groups, including radionuclides such as $^{32}P$ or $^{35}S$, or enzymatic labels such as alkaline phosphatase coupled to the probe via avidin/biotin coupling systems, and the like.

PCR as described U.S. Pat. Nos 4,683,195 and 4,965,188 provide additional uses for oligonucleotides based upon the nucleotide sequences which encode the CBs. Such probes used in PCR may be of recombinant origin, may be chemically synthesized, or a mixture of both. The probe will comprise a discrete nucleotide sequence for the detection of identical sequences or a degenerate pool of possible sequences for identification of closely related genomic sequences.

Other means for producing specific hybridization probes for cb DNAs include the cloning of nucleic acid sequences encoding CBs or CB derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

It is now possible to produce a DNA sequence, or portions thereof, encoding a CB and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a cb sequence or any portion thereof.

The nucleotide sequences may be used to construct an assay to detect activation or induction of the cbs due to inflammation or disease. The nucleotide sequence may be labeled by methods known in the art and added to a fluid or tissue sample from a patient under hybridizing conditions. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye is significantly elevated, the nucleotide sequence has hybridized with the sample, and the assay indicates the presence of the inducing inflammation and/or disease.

The nucleotide sequences for cbs may be used to construct hybridization probes for mapping their respective genomic sequences. The nucleotide sequence provided herein may be mapped to a chromosome or specific regions of a chromosome using well known genetic and/or chromosomal mapping techniques. These techniques include in situ hybridization, linkage analysis against known chromosomal markers, hybridization screening with libraries or flow-sorted chromosomal preparations specific to known chromosomes, and the like. The technique of fluorescent in situ hybridization of chromosome spreads has been described, among other places, in Verma et al (1988) Human Chromosomes: A Manual of Basic Techniques, Pergamon Press, New York N.Y.

Fluorescent in situ hybridization of chromosomal preparations and other physical chromosome mapping techniques may be correlated with additional genetic map data. Examples of genetic map data can be found in the 1994 Genome Issue of Science (265:1981f).

Correlation between the location of a cb on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

The nucleotide sequence encoding CBs may be used to produce purified CBs using well known methods of recombinant DNA technology. Among the many publications that teach methods for the expression of genes after they have been isolated is Goeddel (1990) Gene Expression Technology, Methods and Enzymology, Vol 185, Academic Press, San Diego. CBs may be expressed in a variety of host cells, either prokaryotic or eukaryotic. Host cells may be from the same species from which a particular cb nucleotide sequence was isolated or from a different species. Advantages of producing CBs by recombinant DNA technology include obtaining adequate amounts of the protein for purification and the availability of simplified purification procedures.

Cells transformed with DNA encoding CBs may be cultured under conditions suitable for the expression of cellubrevins and recovery of the proteins from the cell culture. CBs produced by a recombinant cell may be secreted,or they may be contained intracellularly, depending on the particular genetic construction used. In general, it is more convenient to prepare recombinant proteins in secreted form. Purification steps vary with the production process, the host organism and the particular protein produced.

In addition to recombinant production, fragments of CBs may be produced by direct peptide synthesis using solid-phase techniques (cf Stewart et al (1969) Solid-Phase Peptide Synthesis, W H Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431 A Peptide Synthesizer (ABI, Foster City, Calif.) in accordance with the instructions provided by the manufacturer. Various fragments of CBs may be chemically synthesized separately and combined using chemical methods to produce the full length molecule.

CBs for antibody induction do not require biological activity; however, the proteins must be immunogenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small naturally occurring molecules like CBs. Short stretches of CB amino acids may be fused with those of another protein such as keyhole limpet hemocyanin and antibody produced against the chimeric molecule.

Antibodies specific for CBs may be produced by inoculation of an appropriate animal with the polypeptide or an antigenic fragment. An antibody is specific for the particular CB if it is produced against an epitope of the polypeptide and binds to at least part of the natural or recombinant protein. Antibody production includes not only the stimulation of an immune response by injection into animals, but also analogous steps in the production of synthetic antibodies or other specific-binding molecules such as the screening of recombinant immunoglobulin libraries (cf Orlandi R et al (1989) PNAS 86:3833–3837, or Huse W D et al (1989) Science 256:1275–1281) or the in vitro stimulation of lymphocyte populations. Current technology (Winter G and Milstein C (1991) Nature 349:293–299) provides for a number of highly specific binding reagents based on the principles of antibody formation. These techniques may be adapted to produce molecules specifically binding CB.

An additional embodiment of the subject invention is the use of CB specific antibodies, as bioactive agents to treat viral or other infections,; traumatic tissue damage; hereditary diseases such as arthritis or multiple sclerosis; invasive cancers, leukemias and lymphomas; or other physiologic/pathologic problems associated with the induction of CBs and abnormal membrane trafficking.

Bioactive compositions comprising agonists or antagonists of CBs may be administered in a suitable therapeutic dose determined by any of several methodologies including clinical studies on mammalian species to determine maximum tolerable dose and on normal human subjects to determine safe dosage. Additionally, the bioactive-agent may be complexed with a variety of well established compounds or compositions which enhance-stability or pharmacological properties such as half-life. It is contemplated that a therapeutic, bioactive composition may be delivered by intravenous infusion into the bloodstream or any other effective means which could be used.for treatment.

The examples below are provided to illustrate the subject invention. These examples are provided by way of illustration and are not included for the purpose of limiting the invention.

INDUSTRIAL APPLICABILITY

I Isolation of mRNA and Construction of the cDNA Library

The first cellubrevin sequence, CB-1, was identified among the cDNAs (Incyte Clone 80184) comprising the rheumatoid synovium library (SYNORAB01). The synovial joint tissue was obtained from a 68 yr old Caucasian male with rheumatoid arthritis undergoing hip replacement surgery. The frozen tissue was ground in a mortar and pestle and lysed immediately in buffer containing guanidinium isothiocyanate. Lysis was followed by several phenol-chloroform extractions and ethanol precipitations. Poly-$A^+$ mRNA was isolated using biotinylated oligo d(T) and streptavidin coupled to paramagnetic particles (Poly(A) Tract Isolation System, Promega, Madison Wis.). Using this poly-$A^+$ mRNA, a custom cDNA library was constructed by Stratagene (La Jolla Calif.).

The phagemid forms of individual cDNA clones were obtained by the in vivo excision process, in which XL1-BLUE™ cells were coinfected with an f1 helper phage. Proteins derived from both the lambda and f1 helper phages initiated new DNA synthesis from defined sequences on the lambda DNA to create a smaller, single-stranded circular phagemid molecule that includes all the DNA sequence of the pBluescript™ plasmid (Stratagene) and the cDNA insert. The phagemid DNA was released from the cells, purified, and used to reinfect fresh SOLR™ cells (Stratagene), which produced the double-stranded phagemid. Because the phagemid carries the gene for β-lactamase, the newly transformed bacteria were selected on medium containing ampicillin. Phagemid DNA was purified using the QIAWELL-8® Plasmid Purification System (QIAGEN Inc., Chatworth Calif.).

The second cellubrevin cDNA sequence, CB-2, was identified among the cDNAs (Incyte Clone 122826) comprising the human lung library (LUNGNOT01). The lung tissue had been removed from a 72-year-old male during surgery for lung cancer. Although the lung tissue used for LUNGNOT01 did not include any tumor tissue, the patient had smoked approximately 100 packs of cigarettes per year. The cDNA library was purchased from Stratagene (Catalog #STR937210).

The third cellubrevin cDNA sequence, CB-3, was identified among the cDNAs (Incyte Clone 311537) comprising the human lung library (LUNGNOT02). The lung tissue was obtained from a 47 yr old Caucasian male (lot#HEV082 from International Institute for the Advancement of Medicine, Exton Pa.) who died from subarachnoid hemorrhage. The tissue was lysed in a buffer containing GuSCN, and the lysate was centrifuged over a 5.7 M CsCl cushion using an Beckman SW28 rotor in a Beckman L8-70M Ultracentrifuge (Beckman Instruments) for 18 hours at 25,000 rpm at ambient temperature. The RNA was extracted with phenol chloroform pH 8.0, precipitated using 0.3 M sodium acetate and 2.5 volumes of ethanol, resuspended in water and DNase treated for 15 min at 37° C. The RNA was isolated using the Qiagen Oligotex kit (QIAGEN) and used to construct the cDNA library.

First strand cDNA synthesis was accomplished using an oligo d(T) primer/linker which also contained an XhoI restriction site. Second strand synthesis was performed using a combination of DNA polymerase I, E. coli ligase and RNase H, followed by the addition of an EcoRI adaptor to the blunt ended cDNA. The EcoRI adapted, double-stranded cDNA was then digested with XhoI restriction enzyme and fractionated on Sephacryl S400 to obtain sequences which exceeded 1000 bp in size. The size selected cDNAs were inserted into the UniZap® vector system (Stratagene); and the vector, which contains the pBluescript™ phagemid (Stratagene), was transformed into cells of E. coli, strain XL1-BlueMRF™ (Stratagene).

The phagemid forms of individual cDNA clones were obtained by the in vivo excision process. Enzymes from both pBluescript and a cotransformed f1 helper phage nicked the DNA, initiated new DNA synthesis, and created the smaller, single-stranded circular phagemid DNA molecules which contained the cDNA insert. The phagemid DNA was released, purified, and used to reinfect fresh SOLR™ host cells (Stratagene). Presence of the phagemid which carries the gene for β-lactamase allowed transformed bacteria to grow on medium containing ampicillin.

The two lung libraries reflect cDNAs from a diversity of cell types found in the lung. The cell types include but are not limited to pulmonary macrophages, lymphocytes and leukocytes, epithelial and endothelial cells, pulmonary goblet cells and other cells responsible for surfactant associated proteins.

The fourth cellubrevin cDNA sequence, CB-4, was identified among the cDNAs (Incyte Clone 674719) comprising the human cerebellum library (CRBLNOT01). The CRBLNOT01 cDNA library was constructed from normal cerebellum tissue removed from a 69 year old Caucasian male (lot#RT95-05-0301 from the International Institute of Advanced Medicine, Exton Pa.). The frozen tissue was immediately homogenized and cells lysed with a Brinkmann Homogenizer Polytron PT-3000 (Brinkmann Instruments Inc., Westbury N.Y.) in a guanidinium isothiocyanate solution. Lysates were then loaded on a 5.7 M CsCl cushion and ultracentrifuged in a SW28 swinging bucket rotor for 18 hours at 25,000 rpm at ambient temperature. The RNA was extracted once with acid phenol at pH 4.0 and precipitated with 0.3 M sodium acetate and 2.5 volumes of ethanol, resuspended in DEPC-treated water and DNase treated for 25 min at 37° C. The reaction was stopped with an equal volume of pH 8.0 phenol, and the RNA as above. The RNA was isolated using the Qiagen Oligotex kit (QIAGEN) and used to construct the cDNA library.

The RNA was handled according to the recommended protocols in the SuperScript Plasmid System™ for cDNA Synthesis and Plasmid Cloning (Catalog#18248-013; Gibco/BRL). cDNAs were fractionated on a Sepharose CL4B column (Catalog#275105, Pharmacia), and those cDNAs exceeding 400 bp were ligated into pSport I. The plasmid pSport I was subsequently transformed into DH5a™ competent cells (Catalog#18258-012, Gibco/BRL).

II Sequencing of cDNA Clones

The cDNA inserts from random isolates of the various libraries were sequenced by the method of Sanger F and A R Coulson (1975; J Mol Biol 94:441f). Methods for DNA sequencing are well known in the art. Conventional enzymatic methods employed DNA polymerase Klenow fragment, SEQUENASE® (U.S. Biochemical Corp, Cleveland, Ohio) or Taq polymerase to extend DNA chains from an oligonucleotide primer annealed to the DNA template of interest. Methods have been developed for the use of both single- and double-stranded templates. The chain termination reaction products were electrophoresed on urea-acrylamide gels and detected either by autoradiography (for radionuclide-labeled precursors) or by fluorescence (for fluorescent-labeled precursors). Recent improvements in mechanized reaction preparation, sequencing and analysis using the fluorescent detection method have permitted expansion in the number of sequences that can be determined per day (using machines such as the Catalyst 800 or a Hamilton Micro Lab 2200 (Hamilton, Reno Nev.) in combination with four Peltier Thermal Cyclers (PTC200 from M J Research, Watertown Mass.) and the Applied Biosystems 377 or 373 DNA sequencers).

III Homology Searching of cDNA Clones and Deduced Proteins

Each sequence so obtained was compared to sequences in GenBank using a search algorithm developed by Applied Biosystems and incorporated into the INHERIT™ 670 Sequence Analysis System. In this algorithm, Pattern Specification Language (developed by TRW Inc., Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

Alternatively, BLAST, which stands for Basic Local Alignment Search Tool, is used to search for local sequence alignments (Altschul S F (1993) J Mol Evol 36:290–300; Altschul, S F et al (1990) J Mol Biol 215:403–10). BLAST produces alignments of both nucleotide and amino acid sequences to determine sequence similarity. Because of the local nature of the alignments, BLAST is especially useful in determining exact matches or in identifying homologs. Whereas it is ideal for matches which do not contain gaps, it is inappropriate for performing motif-style searching. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

In addition, BLAST analysis was used to search for related molecules within the libraries of the LIFESEQ™ database. This process, an "electronic northern" analysis is analogous to northern blot analysis in that it uses one cellubrevin sequence at a time to search for identical or homologous molecules at a set stringency. The stringency of the electronic northern is based on "product score". The product score is defined as (% nucleotide or amino acid identity [between the query and reference sequences] in Blast multiplied by the % maximum possible BLAST score [based on the lengths of query and reference sequences]) divided by 100. At a product score of 40, the match will be exact within a 1–2% error; and at 70, the match will be exact. Homologous or related molecules can be identified by selecting those which show product scores between approximately 15 and 30.

IV Identification, Full Length Sequencing and Translation of the CBs

Figure 5:
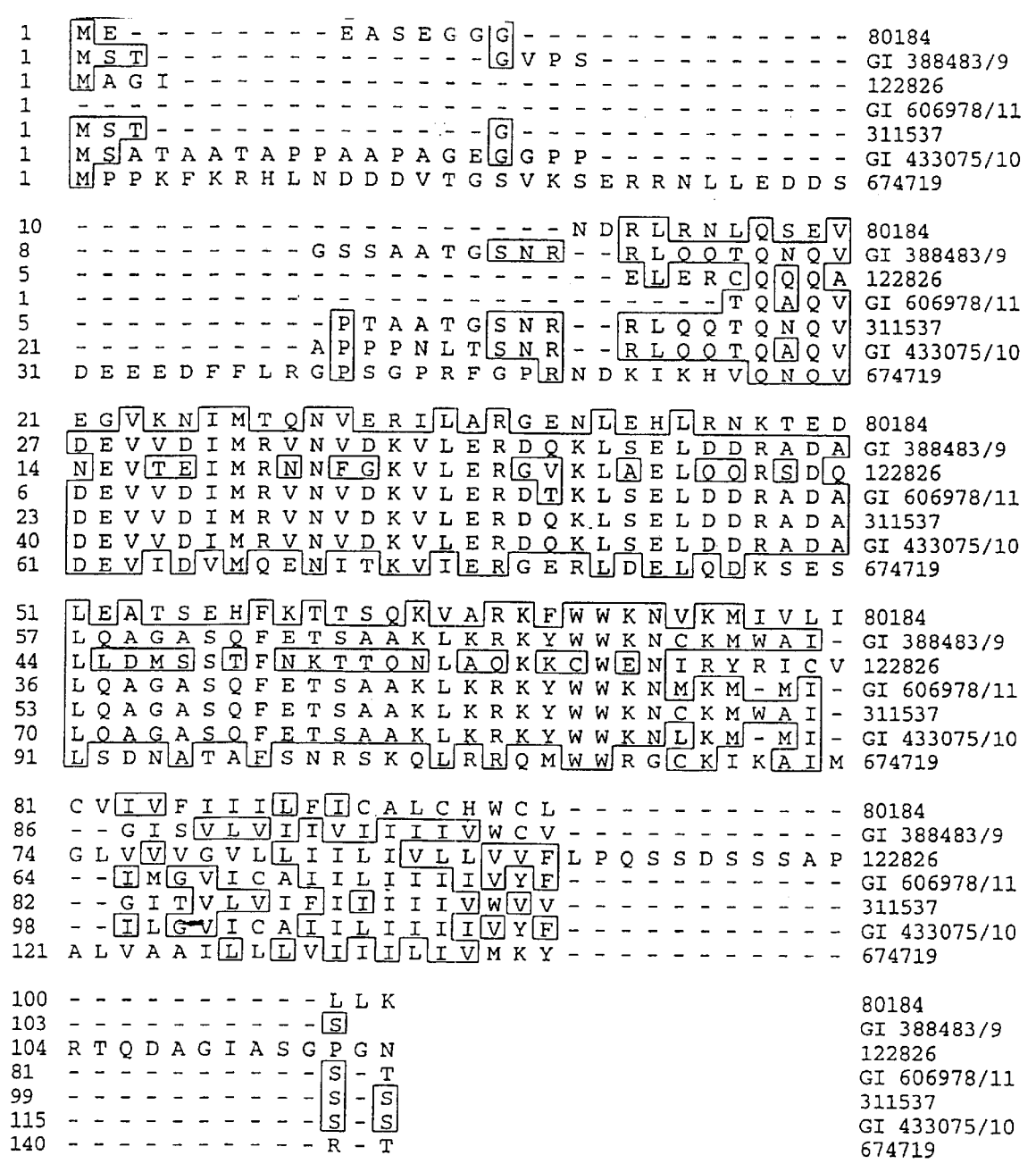

Analysis of the randomly picked and sequenced clones from the rheumatoid synovium library identified the cellubrevin sequence in the Incyte 80184 as homologous to rat cellubrevin (McMahon H T et al (1993) Nature 364:346–9). The cDNA insert comprising Incyte 80184 was fully sequenced using the same methods described above. The coding region of the insert (ATG->TGA) was identified and is shown as SEQ ID NO:1. This sequence for human cb-1 was translated using PatentIN, release 1.30 (an internal United States Patent and Trademark Office software package used to comply with sequence rules and is shown in SEQ ID NO:2. When the translation of the sequence, CB-1, was searched against protein databases such as SwissProt and PIR, no exact matches were found. FIGS. 1–4 show the nucleotide and amino acid sequences of the CBs, disclosed herein. FIG. 5 shows the amino acid alignments of the CB molecules and their most closely related homologs.

Analysis of the randomly picked and sequenced clones from the lung library (LUNGNOT01) identified the cellubrevin sequence in the Incyte 122826 as homologous to Xenopus synaptobrevin (GI 606978; Knecht, A. K. (1988) Proc. Nat. Acad. Sci. 8086–90). The cDNA insert comprising Incyte 122826 was fully sequenced, the coding region of the insert (ATG->TGA) was identified, and it is shown as SEQ ID NO:3. This sequence for human cb-2 was translated using MacDNAsis™ software (Hitachi Software Engineering Co Ltd) and the amino acid sequence is shown in SEQ ID NO:4. When the translation of the sequence, CB-2, was searched against protein databases such as SwissProt and PIR, no exact matches were found.

Analysis of the randomly picked and sequenced portions of clones from the lung library (LUNGNOT02) identified the cellubrevin sequence in the Incyte 122826 as homologous to bovine synaptobrevin (GI 433075; Sudhof T C et al. (1989) Neuron 2:1475–1481). The cDNA insert comprising Incyte 311537 was extended to full length using the method below. Then the coding region of the full length cDNA (ATG->TGA) was identified, and it is shown as SEQ ID NO:5. This sequence-for human cb-3 was translated using MacDNAsis™ software (Hitachi Software Engineering Co Ltd), and the amino acid sequence is shown in SEQ ID NO:6. When the translation of the sequence, CB-3, was searched against protein databases such as SwissProt and PIR, no exact matches were found.

Analysis of the randomly picked and sequenced clones from the cerebellum library (CRBLNOT01) identified the cellubrevin sequence in the Incyte 674719 as a unique, single cellubrevin sequence. This clone appears to represent a new class of induced cellubrevins. The cDNA insert comprising Incyte 674719 was fully sequenced, the coding region of the insert (ATG->TGA) was identified, and the amino acid sequence is shown as SEQ ID NO:7. This sequence for human cb-4 was translated using MacDNAsis™ software (Hitachi Software Engineering Co Ltd) and is shown in SEQ ID NO:8. When the translation of the sequence, CB-4, was searched against protein databases such as SwissProt and PIR, no matches were found.

V Extension of the cDNA of 311537 to Full Length

The partial sequence originally identified in Incyte Clone 311537 was used to design oligonucleotide primers for extension of the cDNAs to full length. Primers are designed based on known sequence; one primer is synthesized to initiate extension in the antisense direction (XLR) and the other to extend sequence in the sense direction (XLF). The primers allow the sequence to be extended "outward" generating amplicons containing new, unknown nucleotide sequence for the gene of interest. The primers may be designed using Oligo 4.0 (National Biosciences Inc, Plymouth Minn.), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The combined lung (catalog #10424-018) and heart (catalog #10419-018) cDNA libraries from GIBCO/BRL (Gaithersburg, Md.) were used with XLR= TGTGTTAGGCAGTAGTGTTTTTTTCTGG and XLF= AATCTGTGATAACAACAGGCTGTGC primers to extend and amplify Incyte Clone 311537 to obtain the full length cellubrevin sequence.

By following the instructions for the XL-PCR kit and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| | |
|---|---|
| Step 1 | 94° C. for 1 min (initial denaturation) |
| Step 2 | 65° C. for 1 min |
| Step 3 | 68° C. for 6 min |
| Step 4 | 94° C. for 15 sec |
| Step 5 | 65° C. for 1 min |
| Step 6 | 68° C. for 7 min |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 µl aliquot of the reaction mixture is analyzed by electrophoresis on a low concentration (about 0.6–0.8%) agarose mini-gel to determine which reactions were successful in extending the sequence. Although all extensions potentially contain a full length gene, some of the largest products or bands are selected and cut out of the gel. Further purification involves using a commercial gel extraction method such as QIAQuick™ (QIAGEN Inc). After recovery of the DNA, klenow enzyme is used to trim single-stranded, nucleotide overhangs creating blunt ends which facilitate religation and cloning.

After ethanol precipitation, the products are redissolved in 13 µl of ligation buffer. Then, 1 µg T4-DNA ligase (15 units) and 1 µl T4 polynucleotide kinase are added, and the mixture is incubated at room temperature for 2–3 hours or overnight at 16° C. Competent E. coli cells (in 40 µl of appropriate media) are transformed with 3 µl of ligation mixture and cultured in 80 µl of SOC medium (Sambrook J et al, supra). After incubation for one hour at 37° C., the whole transformation mixture is plated on Luria Bertani (LB)-agar (Sambrook J et al, supra) containing 2×Carb. The following day, 12 colonies are randomly picked from each plate and cultured in 150 µl of liquid LB/2×Carb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
|--------|---------------------|
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Antisense Analysis

Knowledge of the correct, complete cDNA sequence of any of the CBs disclosed herein enables its use as a tool for antisense technology in the investigation of gene function. Oligonucleotides, either genomic or cDNA fragments comprising the antisense strand of cb, are used either in vitro or in vivo to inhibit expression of the cb mRNA. Such technology is now well known in the art, and probes are designed at various locations along the nucleotide sequences. Cells or whole test animals are treated with such antisense sequences to turn off the cb gene. Frequently, the function of the affected cb is ascertained by observing behavior such as lethality, loss of differentiated function, or changes in morphology at the intracellular, cellular, tissue or organismal level.

In addition to using sequences constructed to interrupt transcription of the open reading frame, modifications of gene expression are obtained by designing antisense sequences to intron regions, promoter/enhancer elements, or even to trans-acting regulatory genes. Similarly, inhibition is achieved using Hogeboom base-pairing methodology, also known as "triple helix" base pairing.

VII Expression of CB

Expression of cb is accomplished by subcloning any of the cbs into appropriate expression vectors and transfecting the vectors into an appropriate host cells. The cloning vector previously used for the generation of the tissue library, either pBluescript or pSport I, also provides for direct expression of the cb sequences in *E. coli*. For example, upstream of the cloning site, pBluescript contains a promoter for β-galactosidase, followed by sequence containing the amino-terminal Met and the subsequent 7 residues of β-galactosidase. Immediately following these eight residues is an engineered bacteriophage promoter useful for artificial priming and transcription and a number of unique restriction sites, including Eco RI, for cloning.

Induction of the isolated, transfected bacterial strain with IPTG using standard methods produces a fusion protein corresponding to the first seven residues of β-galactosidase, about 15 residues of "linker", and the CB peptide encoded by the cDNA. Since cDNA clone inserts are generated by an essentially random process, there is one chance in three that the included cDNA will lie in the correct frame for proper translation. If the cDNA is not in the proper reading frame, it is obtained by deletion or insertion of the appropriate number of bases by well known methods including in vitro mutagenesis, digestion with exonuclease III or mung bean nuclease, or oligonucleotide linker inclusion.

The cb cDNA is shuttled into other vectors known to be useful for expression of protein in specific hosts. Oligonucleotide amplimers containing cloning sites as well as a segment of DNA sufficient to hybridize to stretches at both ends of the target cDNA (25 bases) may be synthesized chemically by standard methods. These primers are then used to amplify the desired gene segments by PCR. The resulting new gene segments are digested with appropriate restriction enzymes under standard conditions and isolated by gel electrophoresis.

Alternately, similar gene segments are produced by digestion of the cDNA with appropriate restriction enzymes and filling in the missing gene segments with chemically synthesized oligonucleotides. Segments of the coding sequence from more than one gene are ligated together and cloned in appropriate vectors to optimize expression of recombinant sequence.

Suitable expression hosts for such chimeric molecules include but are not limited to mammalian cells such as Chinese Hamster Ovary (CHO) and human 293 cells, insect cells such as Sf9 cells, yeast cells such as *Saccharomyces cerevisiae*, and bacteria such as *E. Coli*. For each of these cell systems, a useful expression vector includes an origin of replication to allow propagation in bacteria and a selectable marker such as the β-lactamase antibiotic resistance gene to allow selection in bacteria. In addition, the vectors may include a second selectable marker such as the neomycin phosphotransferase gene useful for the transfection of eukarybtic host cells. Vectors used eukaryotic expression may require RNA processing elements such as 3' polyadenylation sequences if such are not part of the cDNA of interest.

Additionally, the vector may contain promoters or enhancers which increase gene expression. Such promoters are host specific and include MMTV, SV40, or metallothionine promoters for CHO cells; trp, lac, tac or T7 promoters for bacterial hosts, or alpha factor, alcohol oxidase or PGH promoters for yeast. Transcription enhancers, such as the rous sarcoma virus (RSV) enhancer, may be used in mammalian host cells. Once homogeneous cultures of recombinant cells are obtained through standard culture methods, large quantities of recombinantly produced CB are recovered from the conditioned medium and analyzed using chromatographic methods known in the art.

VIII Isolation of Recombinant CBs

Any of the CBs may be expressed as a chimeric protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system. (Immunex Corp., Seattle Wash.). The inclusion of a cleavable linker sequence such as Factor XA or enterokinase (Invitrogen) between the purification domain and the cb sequence is useful to facilitate purification away from the fusion protein.

IX Production of CB Specific Antibodies

Two approaches are utilized to raise antibodies to CBs, and each approach is useful for generating either polyclonal or monoclonal antibodies. In one approach, denatured protein from the reverse phase HPLC separation is obtained in quantities up to 75 mg. This denatured protein are used to immunize mice or rabbits using standard protocols; about 100 micrograms are adequate for immunization of a mouse, while up to 1 mg might be used to immunize a rabbit. For identifying mouse hybridomas, the denatured protein is radioiodinated and used to screen potential murine B-cell hybridomas for those which produce antibody. This procedure requires only small quantities of protein, such that 20 mg would be sufficient for labeling and screening of several thousand clones.

In the second approach, the amino acid sequence of CB, as deduced from translation of the cDNA, is analyzed to determine regions of high immunogenicity. Oligopeptides comprising appropriate hydrophilic regions, as illustrated in FIG. 2, is synthesized and used in suitable immunization protocols to raise antibodies. Analysis to select appropriate epitopes is described by Ausubel F M et al (1989, Current Protocols in Molecular Biology, John Wiley & Sons, New York N.Y.). The optimal amino acid sequences for immunization are usually at the C-terminus, the N-terminus and those intervening, hydrophilic regions of the polypeptide which are likely to be exposed to the external environment when the protein is in its natural conformation.

Typically, selected peptides, about 15 residues in length, are synthesized using an Applied Biosystems Peptide Synthesizer Model 431A using fmoc-chemistry and coupled to keyhole limpet hemocyanin (KLH, Sigma) by reaction with M-maleimidobenzoyl-N-hydroxysuccinimide ester (MBS; cf. Ausubel F M et al, supra). If necessary, a cysteine may be introduced at the N-terminus of the peptide to permit coupling to KLH. Rabbits are immunized with the peptide-KLH complex in complete Freund's adjuvant. The resulting antisera are tested for antipeptide activity by binding the peptide to plastic, blocking with 1% bovine serum albumin, reacting with antisera, washing and reacting with labeled (radioactive or fluorescent), affinity purified, specific goat anti-rabbit IgG.

Hybridomas are prepared and screened using standard techniques. Hybridomas of interest are detected by screening with labeled CB to identify those fusions producing the monoclonal antibody with the desired specificity. In a typical protocol, wells of plates (FAST; Becton-Dickinson, Palo Alto, Calif.) are coated with affinity purified, specific rabbit-anti-mouse (or suitable anti-species Ig) antibodies at 10 mg/ml. The coated wells are blocked with 1% BSA, washed and exposed to supernatants from hybridomas. After incubation the wells are exposed to labeled CB at 1 mg/ml. Clones producing antibodies will bind a quantity of labeled CB which is detectable above background. Such clones are expanded and subjected to 2 cycles of cloning at limiting dilution (1 cell/3 wells). Cloned hybridomas are injected into pristane treated mice to produce ascites, and monoclonal antibody is purified from mouse ascitic fluid by affinity chromatography on Protein A. Monoclonal antibodies with affinities of at least $10^8 M^{-1}$, preferably $10^9$ to $10^{10}$ or stronger, will typically be made by standard procedures as described in Harlow and Lane (1988) Antibodies: A Laboratory Manual. Cold Spring Harbor Laboratory NY; and in Goding (1986) Monoclonal Antibodies: Principles and Practice, Academic Press, New York N.Y., both incorporated herein by reference.

X Diagnostic Test Using CB Specific Antibodies

Particular CB antibodies are useful for investigation of vesicular trafficking or for diagnosis of infectious or hereditary conditions which are characterized by differences in the amount or distribution of a particular CB. Since specific CBs have been found in specific human cDNA libraries, it appears that expression is induced in cells or tissues sharing a common function such as systemic protection.

Diagnostic tests for CBs include methods utilizing the antibody and a label to detect the particular CB in human body fluids, membranes, cells, tissues or extracts of such tissues. The polypeptides and antibodies of the present invention are used with or without modification. Frequently, the polypeptides and antibodies will be labeled by joining them, either covalently or noncovalently, with a substance which provides for a detectable signal. A wide variety of labels and conjugation techniques are known and have been reported extensively in both the scientific and patent literature. Suitable labels include radionuclides, enzymes, substrates, cofactors, inhibitors, fluorescent agents, chemiluminescent agents, magnetic particles and the like. Patents teaching the use of such labels include U.S. Pat. Nos. 3,817,837; 3,850,752; 3,939,350; 3,996,345; 4,277,437; 4,275,149; and 4,366,241. Also, recombinant immunoglobulins may be produced as shown in U.S. Pat. No. 4,816,567, incorporated herein by reference.

A variety of protocols for measuring soluble or membrane-bound CB, using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site monoclonal-based immunoassay utilizing monoclonal antibodies reactive to two non-interfering epitopes on CB is preferred, but a competitive binding assay may be employed. These assays are described, among other places, in Maddox, D E et al (1983, J Exp Med 158:1211).

XI Purification of Natural CBs Using Specific Antibodies

Natural or recombinant CBs are purified by immunoaffinity chromatography using antibodies specific for the particular CB. In general, an immunoaffihity column is constructed by covalently coupling the anti-CB antibody to an activated chromatographic resin.

Polyclonal immunoglobulins are prepared from immune sera either by precipitation with ammonium sulfate or by purification on immobilized Protein A (Pharmacia LKB Biotechnology, Piscataway, N.J.). Likewise, rhonoclonal antibodies are prepared from mouse ascites fluid by ammonium sulfate precipitation or chromatography on immobilized Protein A. Partially purified immunoglobulin is covalently attached to a chromatographic resin such as CnBr-activated Sepharose (Pharmacia LKB Biotechnology). The antibody is coupled to the resin, the resin is blocked, and the derivative resin is washed according to the manufacturer's instructions.

Such immunoaffinity columns are utilized in the purification of CB by preparing cellular fractions from cells containing CB. Such a preparation is derived by solubilization of the whole cell and isolation of subcellular fractions via differential centrifugation, by the addition of detergent, or by other methods well known in the art. Alternatively, a soluble CB containing a signal sequence may be secreted in useful quantity into the medium in which the cells are grown.

A fractionated CB-containing preparation is passed over the immunoaffinity column, and the column is washed under conditions that allow the preferential absorbance of CB (eg, high ionic strength buffers in the presence of detergent). Then, the column is eluted under conditions that disrupt antibody/CB binding (e.g., a buffer of pH 2–3 or a high concentration of a chaotrope such as urea or thiocyanate ion), and CB is collected.

XII Drug Screening

The cellubrevins disclosed in the present invention are particularly useful for screening therapeutic compounds. CBs, or binding fragments thereof, are useful in any of a variety of drug screening techniques. The polypeptide or fragment employed in such a test is either free in solution, affixed to a solid support, borne on a cell surface or located intracellularly. One method of drug screening utilizes eukaryotic or prokaryotic host cells which are stably transformed with recombinant nucleic acids expressing the CB, or a fragment thereof. Drugs are screened against such transformed cells in competitive binding assays. Such cells, either in viable or fixed form, are used for standard binding assays. The formation of complexes between CB and the agent being tested is measured. Alternatively, one may examine the effect of the test agent on complex formation between CB and a receptor is measured.

Thus, the present invention provides methods of screening for drugs or any other agents which affect vesicular trafficking. These methods comprise contacting such an agent with CB polypeptide or a fragment thereof and assaying (i) for the presence of a complex between the agent and the CB polypeptide or fragment, or (ii) for the presence of a complex between the CB polypeptide or fragment and the cell, by methods well known in the art. In such competitive binding assays, the CB polypeptide or fragment is typically labeled. After suitable incubation, free CB polypeptide or fragment is separated from that present in bound form, and the amount of free or uncomplexed label is a measure of the ability of the particular agent to bind to CB or to interfere with the CB and agent complex.

Another technique for drug screening provides high throughput screening for compounds having suitable binding affinity to the CB polypeptides and is described in detail in European Patent Application 84/03564, published on Sep. 13, 1984, incorporated herein by reference. Briefly stated, large numbers of different small peptide test compounds are synthesized on a solid substrate, such as plastic pins or some other surface. The peptide test compounds are reacted with CB polypeptide and washed. Bound CB polypeptide is then detected by methods well known in the art. Purified CB may also be coated directly onto plates for use in the aforementioned drug screening techniques. In addition, non-neutralizing antibodies are used to capture the peptide and immobilize it on the solid support.

This invention also encompasses the use of competitive drug screening assays in which neutralizing antibodies capable of binding CB specifically compete with a test compound for binding to CB polypeptides or fragments thereof. In this manner, the antibodies are used to detect the presence of any peptide which shares one or more antigenic determinants with CB.

XIII Rational Drug Design

The goal of rational drug design is to produce structural analogs of biologically active polypeptides of interest or of small molecules with which they interact, e.g., agonists, antagonists, or inhibitors. Any of these examples are used to fashion drugs which are more active or stable forms of the polypeptide or which enhance or interfere with the function of a polypeptide in vivo (cf. Hodgson J (1991) Bio/Technology 9:19–21, incorporated herein by reference).

In one approach, the three-dimensional structure of a protein of interest, or of a protein-inhibitor complex, is determined by x-ray crystallography, by computer modeling or, most typically, by a combination of the two approaches. Both the shape and charges of the polypeptide are ascertained to elucidate the structure and to determine active site(s) of the molecule. Less often, useful information regarding the structure of a polypeptide is gained by modeling based on the structure of homologous proteins. In both cases, relevant structural information is used to design efficient inhibitors. Useful examples of rational drug design may include molecules which have improved activity or stability as shown by Braxton S and Wells J A (1992 Biochemistry 31:7796–7801) or which act as inhibitors, agonists, or antagonists of native peptides as shown by Athauda S B et al (1993 J Biochem 113:742–746), incorporated herein by reference.

It is also possible to isolate a target-specific antibody, selected by functional assay, as described above, and then to solve the crystal structure. This approach, in principle, yields a pharmacore upon which subsequent drug design may be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id is then used to identify and isolate peptides from banks of chemically or biologically produced peptides. The isolated peptides would then act as the pharmacore.

By virtue of the present invention, a sufficient amount of a particular CB may be made available to perform such analytical studies as X-ray crystallography. In addition, knowledge of the CB amino acid sequence provided herein will provide guidance to those employing computer modeling techniques in place of or in addition to x-ray crystallography.

XIV Identification of Other Members of the VAMP/SNAP/NSF Complex

Purified CBs are research tools for identification, characterization and purification of receptors, docking and fusion proteins. Radioactive labels are incorporated into the CBs by various methods known in the art, and the labelled CB used to identify or capture either soluble or membrane-bound receptor molecules. A preferred method involves labeling the primary amino groups in CB with $^{125}$I Bolton-Hunter reagent (Bolton, A E and Hunter, W M (1973) Biochem J 133: 529). This reagent has been used to label various molecules without concomitant loss of biological activity (Hebert C A et al (1991) J Biol Chem 266: 18989; McColl S et al (1993) J Immunol 150:4550–4555). Receptor-bearing membranes are incubated with the labeled CB molecules, washed to removed unbound molecules, and the receptor-CB complex is quantified. Data obtained using different concentrations of CB are used to calculate values for the number, affinity, and association of receptor-CB complex.

Labeled CB is also useful as a reagent for the purification of a particular molecule with which it interacts. In one embodiment of affinity purification, CB is covalently coupled to a chromatography column. Cells and their membranes are extracted, CB is removed and various CB-free subcomponents are passed over the column. CB-associated molecules bind to the column by virtue of their biological affinity. The CB-complex is recovered from the column, dissociated and the recovered molecule is subjected to N-terminal protein sequencing. This amino acid sequence is then used to identify the captured molecule or to design degenerate oligonucleotide probes for cloning its gene from an appropriate cDNA library.

In another alternate method, monoclonal antibodies are raised against CB and screened to identify those which inhibit the binding of labeled CB. These monoclonal antibodies are then used in affinity purification or expression cloning of associated molecules.

Other soluble binding molecules are identified in a similar manner. Labeled CB is incubated with extracts or biopsied materials derived from cells or tissues such as rheumatoid synovium, lung or cerebellum. After incubation, CB complexes (which are larger than the size of purified CB molecule) are identified by a sizing technique such as size exclusion chromatography or density gradient centrifugation and are purified by methods known in the art. The soluble binding protein(s) are subjected to N-terminal sequencing to obtain information sufficient for database identification, if the soluble protein is known, or for cloning, if the soluble protein is unknown.

XV Use and Administration of Antibodies, Inhibitors, Receptors or Antagonists of CBs Antibodies, inhibitors, receptors or antagonists of CBs (or other treatments to limit vesicular trafficking, TCBs), provide different effects when administered therapeutically. TCBs will be formulated in a nontoxic, inert, pharmaceutically acceptable aqueous carrier medium preferably at a pH of about 5 to 8, more preferably 6 to 8, although the pH may vary according to the characteristics of the antibody, inhibitor, or antagonist being formulated and the condition to be treated. Characteristics of TCBs include solubility of the molecule, half-life and antigenicity/immunogenicity; these and other characteristics may aid in defining an effective carrier. Native human proteins are preferred as TCBs, but organic or synthetic molecules resulting from drug screens may be equally effective in particular situations.

TCBs may be delivered by known routes of administration including but not limited to topical creams and gels; transmucosal spray and aerosol, transdermal patch and bandage; injectable, intravenous and lavage formulations; and orally administered liquids and pills particularly formulated to resist stomach acid and enzymes. The particular formulation, exact dosage, and route of administration will be determined by the attending physician and will vary according to each specific situation.

Such determinations are made by considering multiple variables such as the condition to be treated, the TCB to be administered, and the pharmacokinetic profile of the particular TCB Additional factors which may be taken into account include disease state (e.g. severity) of the patient, age, weight, gender, diet, time of administration, drug combination, reaction sensitivities, and tolerance/response to therapy. Long acting TCB formulations might be administered every 3 to 4 days, every week, or once every two weeks depending on half-life and clearance rate of the particular TCB.

Normal dosage amounts may vary from 0.1 to 100,000 micrograms, up to a total dose of about 1 g, depending upon the route of administration. Guidance as to particular dosages and methods of delivery is provided in the literature; see U.S. Pat. Nos. 4,657,760; 5,206,344; or 5,225,212. It is anticipated that different formulations will be effective for different TCBs and that administration to nerve cells may necessitate delivery in a manner different from that being delivered to vascular endothelial cells.

It is contemplated that conditions or diseases which activate leukocytes may precipitate damage that is treatable with TCBs. These conditions or diseases may be specifically diagnosed by the tests discussed above, and such testing should be performed in suspected cases of viral or other infections, traumatic tissue damage, hereditary diseases such as arthritis or asthma, invasive leukemias and lymphomas; or other physiologic/pathologic problems which deviate from normal cell behavior.

XVI Artificial Vesicles for Delivery of Therapeutic Molecules

The vesicular localization directed by a particular CB and the intracellular and extracellular receptors with which CB interacts is examined using fluorescent antibody. The elucidation of the number, arrangement and specificity of CB in both intracellular and extracellular trafficking is quite valuable. It not only offers the ability to disrupt vesicular processes in the intervention of diseases such as arthritis, asthma, and cystic fibrosis, but also allows for the development of artificial vesicles. These vesicles most resemble liposomes and may be sterically stabilized. The particular cellubrevin which they contain acts as an address to direct the movement of the vesicle into, through or out of the cell. Both the cellubrevin molecule and the contents of the vesicles are carefully selected. These artificial vesicles will have a particular size and the potential to deliver an antibody, nucleotide or another chemotherapeutic molecule such as insulin, DNase, or a therapeutic protein. This technology is also potentially useful for the delivery of vectors and recombinant nucleotides to effect a localized, heritable or nonheritable cell therapy. In any case, the liposome is addressed to a specific cell type, tissue, organ or tumor by the expression of the CB on its surface.

XVI Chimeric, Therapeutic CBs

In another embodiment, the intravesicular end of the CB molecule on an artificial vesicle is chimeric and consists of a therapeutic peptide. The therapeutic peptide is protected within the vesicle during delivery; and at the time of fusion, it is exposed as part of the intracellular plasmalemma. The exposed peptide either carries out its function while still anchored to the membrane or is cleaved at a predetermined sequence by a constitutive intracellular enzyme and released into the interior of the cell. A preferred embodiment of the invention includes the delivery of short therapeutic peptides in this manner.

All publications and patents mentioned in the above specification are herein incorporated by reference. The foregoing written specification is considered to be sufficient to enable one skilled in the art to practice the invention. Indeed, various modifications of the above described modes for carrying out the invention which are obvious to those skilled in the field of molecular biology or related fields are intended to be within the scope of the following claims.

What is claimed is:

1. An isolated polypeptide selected from the group consisting of:

a) a polypeptide comprising an amino acid sequence of SEQ ID NO: 2, SEQ ID NO:4, SEQ ID NO:6 or SEQ ID NO:8;

b) a polypeptide comprising a naturally occurring amino acid sequence at least 90% identical to the amino acid sequence of SEQ ID NO: 2, SEQ ID NO:4, SEQ ID; NO:6 or SEQ ID NO:8, wherein the naturally occurring amino acid sequence has membrane trafficking activity, and c) an immunogenic fragment of a polypeptide having the amino acid sequence of SEQ ID NO: 2, SEQ ID NO:4, SEQ ID NO:6 or SEQ ID NO:8.

2. An isolated polypeptide of claim 1, comprising the sequence of SEQ ID NO:4.

3. An isolated polypeptide of claim 1, comprising the sequence of SEQ ID NO:6.

4. An isolated polypeptide of claim 1, comprising the sequence of SEQ ID NO:8.

5. A method for producing a polypeptide of claim 1, the method comprising:
   a) culturing a cell under conditions suitable for expression of the polypeptide, wherein said cell is transformed with a recombinant polynucleotide, and said recombinant polynucleotide comprises a promoter sequence operably linked to a polynucleotide encoding the polypeptide of claim 1, and
   b) recovering the polypeptide so expressed.

6. The method of claim 5, wherein the polypeptide comprises the sequence of SEQ ID NO:4.

7. The method of claim 5, wherein the polypeptide comprises the sequence of SEQ ID NO:6.

8. The method of claim 5, wherein the polypeptide comprises the sequence of SEQ ID NO:8.

9. A composition comprising a polypeptide of claim 1 and a pharmaceutically acceptable excipient.

10. A composition of claim 9, wherein the polypeptide comprises the amino acid sequence of SEQ ID NO:4.

11. A composition of claim 9, wherein the polypeptide comprises the amino acid sequence of SEQ ID NO:6.

12. A composition of claim 9, wherein the polypeptide comprises the amino acid sequence of SEQ ID NO:8.

13. A method for screening a compound for effectiveness as an agonist of a polypeptide of claim 1, the method comprising:
   a) exposing a sample comprising a polypeptide of claim 1 to a compound, and
   b) detecting agonist activity in the sample.

14. A method for screening a compound for effectiveness as an antagonist of a polypeptide of claim 1, the method comprising:
   a) exposing a sample comprising a polypeptide of claim 1 to a compound, and
   b) detecting antagonist activity in the sample.

15. A method of screening for a compound that specifically binds to a polypeptide of claim 1, said method comprising:
   a) combining the polypeptide of claim 1 with at least one test compound under suitable conditions, and
   b) detecting binding of the polypeptide of claim 1 to the test compound, thereby identifying a compound that specifically binds to the polypeptide of claim 1.

16. A method of screening for a compound that modulates the activity of a polypeptide of claim 1, said method comprising:
   a) combining a polypeptide of claim 1 with at least one test compound under conditions permissive for the activity of the polypeptide of claim 1,
   b) assessing the activity of the polypeptide of claim 1 in the presence of the test compound, and
   c) comparing the activity of the polypeptide of claim 1 in the presence of the test compound with the activity of the polypeptide of claim 1 in the absence of the test compound, wherein a change in the activity of the polypeptide of claim 1 in the presence of the test compound is indicative of a compound that modulates the activity of the polypeptide of claim 1.

* * * * *

SEQUENCE LISTING (1) GENERAL INFORMATION:

(iii) NUMBER OF SEQUENCES: 51

(2) INFORMATION FOR SEQ ID NO:1:

(i) SEQUENCE CHARACTERISTICS:
      (A) LENGTH: 309 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: SYNORAB01
      (B) CLONE: 80814

(xi) SEQUENCE DESCRIPTION: SEQ ID NO:1:

```
ATGGAGGAAG CCAGTGAAGG TGGAGGAAAT GATCGTTTGC GGAACCTGCA AAGTGAGGTG    60

GAGGGAGTTA AGAATATTAT GACCCAGAAT GTGGAGCGGA TCCTGGCCCG GGGGGAAAAC   120

TTGGAACATC TCCGCAACAA GACAGAGGAT CTGGAAGCCA CATCTGAGCA CTTCAAGACG   180

ACATCGCAGA AGGTGGCTCG AAAATTCTGG TGGAAGAACG TGAAGATGAT TGTCCTTATC   240

TGCGTGATTG TTTTTATCAT CATCCTCTTC ATTTGTGCTC TTTGCCACTG GTGCCTTCTT   300

CTTAAGTAA                                                          309
```

(2) INFORMATION FOR SEQ ID NO:2:

(i) SEQUENCE CHARACTERISTICS:
      (A) LENGTH: 102 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY: SYNORBAB01
      (B) CLONE: 80814

(xi) SEQUENCE DESCRIPTION: SEQ ID NO:2:

```
Met Glu Glu Ala Ser Glu Gly Gly Gly Asn Asp Arg Leu Arg Asn Leu
 1               5                  10                  15

Gln Ser Glu Val Glu Gly Val Lys Asn Ile Met Thr Gln Asn Val Glu
            20                  25                  30

Arg Ile Leu Ala Arg Gly Glu Asn Leu Glu His Leu Arg Asn Lys Thr
        35                  40                  45

Glu Asp Leu Glu Ala Thr Ser Glu His Phe Lys Thr Thr Ser Gln Lys
    50                  55                  60

Val Ala Arg Lys Phe Trp Trp Lys Asn Val Lys Met Ile Val Leu Ile
65                  70                  75                  80

Cys Val Ile Val Phe Ile Ile Ile Leu Phe Ile Cys Ala Leu Cys His
                85                  90                  95

Trp Cys Leu Leu Leu Lys
            100
```

(2) INFORMATION FOR SEQ ID NO:3:

(i) SEQUENCE CHARACTERISTICS:
      (A) LENGTH: 351 base pairs (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT01
        (B) CLONE: 122826

(xi) SEQUENCE DESCRIPTION: SEQ ID NO:3:

```
ATGGCAGGAA TAGAGTTGGA GCGGTGCCAG CAGCAGGCGA ATGAGGTGAC GGAAATTATG      60

CGTAACAACT TCGGCAAGGT CCTGGAGCGT GGTGTGAAGC TGGCCGAACT GCAGCAGCGT     120

TCAGACCAAC TCCTGGATAT GAGCTCAACC TTCAACAAGA CTACACAGAA CCTGGCCCAG     180

AAGAAGTGCT GGGAGAACAT CCGTTACCGG ATCTGCGTGG GGCTGGTGGT GGTTGGTGTC     240

CTGCTCATCA TCCTGATTGT GCTGCTGGTC GTCTTTCTCC CTCAGAGCAG TGACAGCAGT     300

AGTGCCCCAC GGACCCAGGA TGCAGGCATT GCCTCAGGGC CTGGGAACTG A              351
```

(2) INFORMATION FOR SEQ ID NO:4:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: LUNGNOT01
        (B) CLONE: 122826

(xi) SEQUENCE DESCRIPTION: SEQ ID NO:4:

```
Met Ala Gly Ile Glu Leu Glu Arg Cys Gln Gln Gln Ala Asn Glu Val
 1               5                  10                  15

Thr Glu Ile Met Arg Asn Asn Phe Gly Lys Val Leu Glu Arg Gly Val
                20                  25                  30

Lys Leu Ala Glu Leu Gln Gln Arg Ser Asp Gln Leu Leu Asp Met Ser
            35                  40                  45

Ser Thr Phe Asn Lys Thr Thr Gln Asn Leu Ala Gln Lys Lys Cys Trp
        50                  55                  60

Glu Asn Ile Arg Tyr Arg Ile Cys Val Gly Leu Val Val Val Gly Val
65                  70                  75                  80

Leu Leu Ile Ile Leu Ile Val Leu Leu Val Val Phe Leu Pro Gln Ser
                85                  90                  95

Ser Asp Ser Ser Ser Ala Pro Arg Thr Gln Asp Ala Gly Ile Ala Ser
            100                 105                 110

Gly Pro Gly Asn
        115
```

(2) INFORMATION FOR SEQ ID NO:5:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT02
        (B) CLONE: 311537

(xi) SEQUENCE DESCRIPTION: SEQ ID NO:5:

```
ATGTCTACAG GTCCAACTGC TGCCACTGGC AGTAATCGAA GACTTCAGCA GACACAAAAT    60

CAAGTAGATG AGGTGGTGGA CATAATGCGA GTTAACGTGG ACAAGGTTCT GGAAAGAGAC   120

CAGAAGCTCT CTGAGTTAGA CGACCGTGCA GACGCACTGC AGGCAGGCGC TTCTCAATTT   180

GAAACGAGCG CAGCCAAGTT GAAGAGGAAA TATTGGTGGA AGAACTGCAA GATGTGGGCA   240

ATCGGGATTA CTGTTCTGGT TATCTTCATC ATCATCATCA TCGTGTGGGT TGTCTCTTCA   300

TGA                                                                 303
```

(2) INFORMATION FOR SEQ ID NO:6:

(i) SEQUENCE CHARACTERISTICS:
        (A) LENGTH: 100 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: LUNGNOT02
        (B) CLONE: 311537

(xi) SEQUENCE DESCRIPTION: SEQ ID NO:6:

```
Met Ser Thr Gly Pro Thr Ala Ala Thr Gly Ser Asn Arg Arg Leu Gln
 1               5                  10                  15

Gln Thr Gln Asn Gln Val Asp Glu Val Val Asp Ile Met Arg Val Asn
                20                  25                  30

Val Asp Lys Val Leu Glu Arg Asp Gln Lys Leu Ser Glu Leu Asp Asp
            35                  40                  45

Arg Ala Asp Ala Leu Gln Ala Gly Ala Ser Gln Phe Glu Thr Ser Ala
        50                  55                  60

Ala Lys Leu Lys Arg Lys Tyr Trp Trp Lys Asn Cys Lys Met Trp Ala
65                  70                  75                  80

Ile Gly Ile Thr Val Leu Val Ile Phe Ile Ile Ile Ile Val Trp
                85                  90                  95

Val Val Ser Ser
            100
```

(2) INFORMATION FOR SEQ ID NO:7:

(i) SEQUENCE CHARACTERISTICS:
        (A) LENGTH: 426 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: CRBLNOT01
        (B) CLONE: 604719

(xi) SEQUENCE DESCRIPTION: SEQ ID NO:7:

```
ATGCCTCCCA AGTTTAAGCG CCACCTCAAT GATGATGATG TCACAGGTTC TGTGAAAAGT    60

GAAAGGAGAA ATCTTTTGGA AGATGATTCA GATGAAGAAG AGGACTTTTT TCTAAGGGGA   120

CCATCTGGAC CAAGATTTGG ACCTAGAAAT GATAAAATTA GCATGTTCAA GAATCAAGTG   180

GATGAAGTTA TTGATGTCAT GCAAGAAAAT ATTACAAAGG TAATTGAGAG AGGGGAGAGA   240

CTAGATGAAC TACAGGACAA ATCAGAAAGC TTATCGGATA ATGCAACAGC TTTTAGCAAC   300
```

```
AGATCCAAAC AACTTCGAAG GCAAATGTGG TGGCGTGGAT GCAAAATAAA AGCCATCATG    360

GCTTTGGTTG CTGCTATCCT TTTGCTAGTG ATTATCATTC TTATAGTCAT GAAATACCGT    420

ACTTGA                                                                426
```

(2) INFORMATION FOR SEQ ID NO:8:

(i) SEQUENCE CHARACTERISTICS:
        (A) LENGTH: 141 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: CRBLNOT01
        (B) CLONE: 604719

(xi) SEQUENCE DESCRIPTION: SEQ ID NO:8:

```
Met Pro Pro Lys Phe Lys Arg His Leu Asn Asp Asp Val Thr Gly
 1               5                  10                  15

Ser Val Lys Ser Glu Arg Arg Asn Leu Leu Glu Asp Asp Ser Asp Glu
                20                  25                  30

Glu Glu Asp Phe Phe Leu Arg Gly Pro Ser Gly Pro Arg Phe Gly Pro
            35                  40                  45

Arg Asn Asp Lys Ile Lys His Val Gln Asn Gln Val Asp Glu Val Ile
    50                  55                  60

Asp Val Met Gln Glu Asn Ile Thr Lys Val Ile Glu Arg Gly Glu Arg
65                  70                  75                  80

Leu Asp Glu Leu Gln Asp Lys Ser Glu Ser Leu Ser Asp Asn Ala Thr
                85                  90                  95

Ala Phe Ser Asn Arg Ser Lys Gln Leu Arg Arg Gln Met Trp Trp Arg
            100                 105                 110

Gly Cys Lys Ile Lys Ala Ile Met Ala Leu Val Ala Ala Ile Leu Leu
        115                 120                 125

Leu Val Ile Ile Ile Leu Ile Val Met Lys Tyr Arg Thr
    130                 135                 140
```

(2) INFORMATION FOR SEQ ID NO:9:

(i) SEQUENCE CHARACTERISTICS:
        (A) LENGTH: 103 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GENBANK
        (B) CLONE: GI 388483

(xi) SEQUENCE DESCRIPTION: SEQ ID NO:9:

```
Met Ser Thr Gly Val Pro Ser Gly Ser Ser Ala Ala Thr Gly Ser Asn
 1               5                  10                  15

Arg Arg Leu Gln Gln Thr Gln Asn Gln Val Asp Glu Val Val Asp Ile
                20                  25                  30

Met Arg Val Asn Val Asp Lys Val Leu Glu Arg Asp Gln Lys Leu Ser
            35                  40                  45

Glu Leu Asp Asp Arg Ala Asp Ala Leu Gln Ala Gly Ala Ser Gln Phe
    50                  55                  60
```

```
Glu Thr Ser Ala Ala Lys Leu Lys Arg Lys Tyr Trp Trp Lys Asn Cys
 65                  70                  75                  80

Lys Met Trp Ala Ile Gly Ile Ser Val Leu Val Ile Ile Val Ile Ile
                 85                  90                  95

Ile Ile Val Trp Cys Val Ser
            100
```

(2) INFORMATION FOR SEQ ID NO:10:

(i) SEQUENCE CHARACTERISTICS:
        (A) LENGTH: 116 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GENBANK
        (B) CLONE: GI 433075

(xi) SEQUENCE DESCRIPTION: SEQ ID NO:10:

```
Met Ser Ala Thr Ala Ala Thr Ala Pro Pro Ala Ala Pro Ala Gly Glu
 1               5                  10                  15

Gly Gly Pro Pro Ala Pro Pro Pro Asn Leu Thr Ser Asn Arg Arg Leu
                 20                  25                  30

Gln Gln Thr Gln Ala Gln Val Asp Glu Val Val Asp Ile Met Arg Val
             35                  40                  45

Asn Val Asp Lys Val Leu Glu Arg Asp Gln Lys Leu Ser Glu Leu Asp
 50                  55                  60

Asp Arg Ala Asp Ala Leu Gln Ala Gly Ala Ser Gln Phe Glu Thr Ser
 65                  70                  75                  80

Ala Ala Lys Leu Lys Arg Lys Tyr Trp Trp Lys Asn Leu Lys Met Met
                 85                  90                  95

Ile Ile Leu Gly Val Ile Cys Ala Ile Ile Leu Ile Ile Ile Ile Val
                100                 105                 110

Tyr Phe Ser Ser
        115
```

(2) INFORMATION FOR SEQ ID NO:11:

(i) SEQUENCE CHARACTERISTICS:
        (A) LENGTH: 82 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GENBANK
        (B) CLONE: GI 606978

(xi) SEQUENCE DESCRIPTION: SEQ ID NO:11:

```
Thr Gln Ala Gln Val Asp Glu Val Val Asp Ile Met Arg Val Asn Val
 1               5                  10                  15

Asp Lys Val Leu Glu Arg Asp Thr Lys Leu Ser Glu Leu Asp Asp Arg
                 20                  25                  30

Ala Asp Ala Leu Gln Ala Gly Ala Ser Gln Phe Glu Thr Ser Ala Ala
             35                  40                  45

Lys Leu Lys Arg Lys Tyr Trp Trp Lys Asn Met Lys Met Met Ile Ile
 50                  55                  60
```

```
Met Gly Val Ile Cys Ala Ile Ile Leu Ile Ile Ile Val Tyr Phe
 65                  70                  75                  80

Ser Thr
```

(2) INFORMATION FOR SEQ ID NO:12:

(i) SEQUENCE CHARACTERISTICS:
        (A) LENGTH: 196 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: KIDNNOT02
        (B) CLONE: 193493

(xi) SEQUENCE DESCRIPTION: SEQ ID NO:12:

```
GGCGAATTCA CTTATTGATN GGCTGGGATG CTCNGAGANA TGGAGNAAGC AGTGAAGNTG     60

GAGGAAATGA TCGTNTGCGG AANCTCCAAA GTGAGNTGGA GGGAGTTAAG AATATTATGN    120

CNCAGAATGT GGAGCGGATC ATGGCCCGNG GGGAAAACTT NGAATATCTC CGCAAAAAGN    180

TAGAGGATAT NGNAGC                                                   196
```

(2) INFORMATION FOR SEQ ID NO:13:

(i) SEQUENCE CHARACTERISTICS:
        (A) LENGTH: 92 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: MPHGNOT02
        (B) CLONE: 204520

(xi) SEQUENCE DESCRIPTION: SEQ ID NO:13:

```
CTGAGACATG GAGGAAGCCA GTTAAGGTNG AGGAAATGAT CGTNTGCGGA ACCTNCAAAG     60

TNAGGTGGAG TGNGTTAAGA ATATTATGAC CC                                  92
```

(2) INFORMATION FOR SEQ ID NO:14:

(i) SEQUENCE CHARACTERISTICS:
        (A) LENGTH: 98 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: MPHGNOT02
        (B) CLONE: 204536

(xi) SEQUENCE DESCRIPTION: SEQ ID NO:14:

```
CTGAGACATG GAGGAAGCCA GTGAAGGTGG AGGAAATGAT CGTNTGCGGA ACCTGCAAAG     60

TGAGGTNGAG GGAGTTAAGA ATATTATGAC CCAGAATT                            98
```

(2) INFORMATION FOR SEQ ID NO:15:

(i) SEQUENCE CHARACTERISTICS:
        (A) LENGTH: 223 base pairs
        (B) TYPE: nucleic acid

```
        (C) STRANDEDNESS: single
        (D) TOPOLOGY: linear (ii) MOLECULE TYPE: cDNA (vii) IMMEDIATE SOURCE:
        (A) LIBRARY: SINTNOT02
        (B) CLONE: 232343

(xi) SEQUENCE DESCRIPTION: SEQ ID NO:15:

GGCGAATTCA CTTACTGACC GGCCTGGGCT GCTCTGAGAC ATGGAGGAAG CCAGTNAAGG      60

TGGAGGAAAT GATCGTNTGC GGAACCTGCA AAGTGAGGTG GAGGGAGTTA AGAATATTAT     120

GACCCAGAAT NTGGAGCGGA TCCTGGCCCN GGGGGAAAAC TTGGAACATC TCCGCAACAA     180

GACAGAGGAT CTGGAAGCCA CATCTGAGCA CTTCAAGACG ACA                       223

(2) INFORMATION FOR SEQ ID NO:16:

(i) SEQUENCE CHARACTERISTICS:
        (A) LENGTH: 241 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SINTNOT02
        (B) CLONE: 237196

(xi) SEQUENCE DESCRIPTION: SEQ ID NO:16:

GCGGAACCTG CAAAGTGAGG TGGAGGGAGT TAAGAATATT ATGACCCAGA ATGTGGAGCG      60

GNTCCTGGCC CGGGGGGAAA ACTTGGAACA TCTCCGCAAC AAGACAGAGG ATCTGGAAGC     120

CACATCTGAG CACTTCAAGA CGACATCGCA GAAGGTGGCT CGAAAATTCT GGTGGAAGAA     180

CGTGAAGATG ATTGTCCTTA TCTGCGTGAT TGTTTTTATC ATCATCCTCT TCATTGTGCT     240

G                                                                    241

(2) INFORMATION FOR SEQ ID NO:17:

(i) SEQUENCE CHARACTERISTICS:
        (A) LENGTH: 97 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: EOSIHET02
        (B) CLONE: 288770

(xi) SEQUENCE DESCRIPTION: SEQ ID NO:17:

CTCGTGCCGA ATTCGGCAGA GNTGAACTAG AGGGCCCAGC ATGTGGCTGG GAAACTTTTG      60

GTGGCCAGTG GGTAATAAAG ACCNTTCAGT ATGCCCT                               97

(2) INFORMATION FOR SEQ ID NO:18:

(i) SEQUENCE CHARACTERISTICS:
        (A) LENGTH: 186 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
```

(A) LIBRARY: LUNGNOT02
        (B) CLONE: 312955

(xi) SEQUENCE DESCRIPTION: SEQ ID NO:18:

CANGAGCTGC TGCCANGTTG TATGCCCCAG AAGGTACCTT GGTCCCCCGG AAGGAGAGAA    60

AAAAGAGAGA TGGACTGTGG CTGCATTTCT TGGGTCCTTA GAGTGGGCTN GAGAGACCTG   120

AGGGCCCAGN ATGTGGCTGG GAAANTNTTG GTGGCCATGG GTAATAAANN CCCTTCAGTA   180

TCCCTA                                                              186

(2) INFORMATION FOR SEQ ID NO:19:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: PROSNOT01
        (B) CLONE: 361833

(xi) SEQUENCE DESCRIPTION: SEQ ID NO:19:

TGGCTCGAAA ATTCTGGTGG AAGAACGTGA AGATGATTGT CCTTATCTGC GTGATTGTTT    60

TTATCATNAT CCTCTTCATT GTGCTCTTTG CCACTGGTGC CTTCTCTTAA GTAACAGGGA   120

ACCTCTCCCA CCTGCCCTTC TCTTCAGGGA CAACCCTCCA TAAATGTGTG CCAAGAGGGT   180

CTCCTTTCCT GTCTTCCTCT ACAGAGAATG CTGCTCGGTC CTCCTACCCC TCTTCCCGAG   240

GCCCTGCTGC T                                                        251

(2) INFORMATION FOR SEQ ID NO:20:

(i) SEQUENCE CHARACTERISTICS:
        (A) LENGTH: 284 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SYNORAT01
        (B) CLONE: 370165

(xi) SEQUENCE DESCRIPTION: SEQ ID NO:20:

TAGGCGNAAT TCACTTACTG AACGGACTGN GNTGNTCTGN GACATGGTGG AAGCCAGTGN    60

AGGTGGAGGA AATGATCGTG TGCGGAACCT GCAAAGTGAG GTGGAGGGAG TTAAGAATAT   120

TATGACCCAG AATGTGGAGC GGATCCTGGC CCGNGGGGAA AACTTGGAAN ATCTCCGCAA   180

CAAGACAGAG GATCTGGAAG CCACATCTGA GCACTTCAAG ACGACATCGC AGAAGGTGGC   240

TCGAAAATTC TGGTGGAAGA ACGTGAAGAT GATTGTCCTT ATCT                    284

(2) INFORMATION FOR SEQ ID NO:21:

(i) SEQUENCE CHARACTERISTICS:
        (A) LENGTH: 182 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:

(A) LIBRARY: LUNGNOT02
        (B) CLONE: 371304

(xi) SEQUENCE DESCRIPTION: SEQ ID NO:21:

CTGCTGCCAC GTTGTATGCC CCAGAAGGTA CCTTGGTCCC CCGGAAGGAG AGAAAAAAGA    60

GAGATGGACT GTGGCTGCAT TTCTTGGGTC CTTAGAGTGG GCTGGAGAGA CCTAGAGGGC   120

CCAGCATGTG GCTGGGAAAC TGTTGGTGGC CAGTGGGTAA TAAAGACCTT TCAGTATCCC   180

TA                                                                 182

(2) INFORMATION FOR SEQ ID NO:22:

(i) SEQUENCE CHARACTERISTICS:
        (A) LENGTH: 174 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: THYMNOT02
        (B) CLONE: 388852

(xi) SEQUENCE DESCRIPTION: SEQ ID NO:22:

GCCATGTTGG TATGCCCCAG AAGGTACCTT GGTCCCCCGG AAGGAGAGAA AAAGAGAGA    60

TGGACTGTGG CTGCATTTCT TGGGTCCTTA GAGTGGGCTG GAGAGACCTA GGAGGGCCCA   120

GCATGTGGCT GGGAAACTGT TGGTGGCCAG TGGGTAATAA AGACCTTTCA GTAT         174

(2) INFORMATION FOR SEQ ID NO:23:

(i) SEQUENCE CHARACTERISTICS:
        (A) LENGTH: 247 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: TMLR3DT01
        (B) CLONE: 401907

(xi) SEQUENCE DESCRIPTION: SEQ ID NO:23:

AGCGGATCCT GGCCCGGGGG GAAAACTTGG AACATCTNCG CAACAAGACA GAGGNTCTGG    60

AAGCCACATC TGAGCANTTC AAGACGNCAT CGCAGAAGGT GGCTCGAAAA TTCTGGTGGA   120

AGAACGTGAA GATGATTGTN CTTATCTGCG TGATTNTTTT TATCATCATC CTCTTNATTG   180

TGCTCTTTGC CACTGGTGCC TTCTCTTAAG TAACAGGGGA CCTNTCCCAC CTGCCCTTCT   240

CTTCAGG                                                            247

(2) INFORMATION FOR SEQ ID NO:24:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: MMLR2DT01
        (B) CLONE: 478156

(xi) SEQUENCE DESCRIPTION: SEQ ID NO:24:

```
GCCGACTAGG CGAATTCACT TACTGACCGG CCTGGGCTGC TCTGAGACAT GGAGGAAGCC    60

AGTGAAGGTG GAGGAAATGA TCGTGTGCGG AACCTGCAAA GTGAGGTGGA GGGAGTTAAG   120

AATATTATGA CCCAGAATGT GGAGCGGATC CTGGCCCGGG GGGAAAACTT GGAACATCTC   180

CGCAACAAGA CAGAGGATCT GGAAGCCACA TCTGAGCACT TCAAGACGAC ATCGCAGAAG   240

GTGGCTCGAA AATTCTT                                                 257
```

(2) INFORMATION FOR SEQ ID NO:25:

(i) SEQUENCE CHARACTERISTICS:
        (A) LENGTH: 244 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: TMLR3DT02
        (B) CLONE: 503375

(xi) SEQUENCE DESCRIPTION: SEQ ID NO:25:

```
TAGGCGAATT CACTTACTGA CCGGCCTGGG CTGCTCTGAG ACATGGAGGA AGCCAGTGAA    60

GGTGGAGGAA ATGATCGTGT GCGGAACCTG CAAAGTGAGG TGGAGGGAGT TAAGAATATT   120

ATGACCCAGA ATGTGGAGCG GATCCTGGCC CGGGGGGAAA ACTTGGAACA TCTCCGCAAC   180

AAGACAGAGG ATCTGGAAGC CACATCTGAG CACTTCAAGA CGACATCGCA GAAGGTGGCT   240

CGAA                                                               244
```

(2) INFORMATION FOR SEQ ID NO:26:

(i) SEQUENCE CHARACTERISTICS:
        (A) LENGTH: 257 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: BRSTTUT01
        (B) CLONE: 604145

(xi) SEQUENCE DESCRIPTION: SEQ ID NO:26:

```
CTCCCACCTG CCCTTNTCTT CAGGGACAAC CCTCCATAAA TGTGTGCCAA GAGGGTCTNC    60

TTTCCTGTCT TCCTCTACAG AGAATGCTGC TCGGTCCTCC TACCCCTNTT CCCGAGGCCC   120

TGTTGCCATG TTGTATGCCC CAGAAGGTAC CTTGGTCCCC CGGAAGGAGA GAAAAAAGAG   180

AGATGGACTG TGGCTGCATT TCTTGGGTCC TTAGAGTGGG CTGGAGAGAC CTAGAGGGCC   240

CAGCATGTGG CTNGGAA                                                 257
```

(2) INFORMATION FOR SEQ ID NO:27:

(i) SEQUENCE CHARACTERISTICS:
        (A) LENGTH: 277 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: KIDNNOT05
        (B) CLONE: 628038

(xi) SEQUENCE DESCRIPTION: SEQ ID NO:27:

GNGGATCCTG GNCCGGGGGG AAAACTTGGA ACATCTNCGC AACAAGACAG AGGATCTGGA    60

AGCCACATCT GAGCACTTCA AGACGACATC GCAGAAGGTG GCTCGGAAAT TCTGGTGGAA    120

GAACGTGAAG ATGNTTGTCC TTATCTGCGT GATTGTTTTT ATCATCATCC TCTTCATTGT    180

GCTCTTTGCC ACTGGTGCCT TCTNTTAAGT AACAGGGAAC CTCTNCCACC TGCCCTTCTT    240

TTCAGGGACA ACCCTCCATA AATGTGTGCC AAGAGGG                             277

(2) INFORMATION FOR SEQ ID NO:28:

(i) SEQUENCE CHARACTERISTICS:
        (A) LENGTH: 258 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SYNORAT04
        (B) CLONE: 705485

(xi) SEQUENCE DESCRIPTION: SEQ ID NO:28:

GGGAGGAAGC CGACTAGGCG AATTCACTTA CTGACCGGCC TGGGCTGCTC TGAGACATGG    60

AGGAAGCCAG TGAAGGTGGA GGAAATGATC GTGTGCGGAA CCTGCAAAGT GAGGTGGAGG    120

GAGTTAAGAA TATTATGACC CAGAATGTGG AGCGGATCCT GGCCCGGGGG GAAAACTTGG    180

AACATCTCCG CAACAAGACA GAGGATCTNG AAGCCACATC TGAGCACTTC AAGACGACAT    240

CGCAGAAGGT GGCTCGAA                                                  258

(2) INFORMATION FOR SEQ ID NO:29:

(i) SEQUENCE CHARACTERISTICS:
        (A) LENGTH: 238 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SYNORAT04
        (B) CLONE: 709709

(xi) SEQUENCE DESCRIPTION: SEQ ID NO:29:

GGAGGAAGCC GACTAGGCGA ATTCACTTAC TGACCGGCCT GGGCTGCTCT GAGACATGGA    60

GGAAGCCAGT GAAGGTGGAG GAAATGATCG TGTGCGGAAC CTGCAAAGTG AGGTGGAGGG    120

AGTTAAGAAT ATTATGACCC AGAATNTGGA GCGGATCCTG GCCCGGGGG AAAACTTNGA     180

ACATCTTCGN AACAAGACAG AGGATCTTGA AGNCACATCT NAGCACTTNA AGACGGCA     238

(2) INFORMATION FOR SEQ ID NO:30:

(i) SEQUENCE CHARACTERISTICS:
        (A) LENGTH: 242 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: TONSNOT01
        (B) CLONE: 734929

(xi) SEQUENCE DESCRIPTION: SEQ ID NO:30:

GAGACATGGA GGAAGCCAGT GAAGGTGGAG GAAATGATCG TGTGCGGAAC CTGCAAAGTG    60

AGGTGGAGGG AGTTAAGAAT ATTATGACCC AGAATGTGGA GCGGATCCTG GCCCGGGGGG    120

AAAACTTGGA ACATCTCCGC AATAAGACAG AGGATCTGGA AGCCACATCT GAGCACTTCA    180

AGACGACATC GCAGAAGGTG GCTCGGAAAT TCTGGTGGAA GAACGTGAAG ATGATTGTNC    240

TT    242

(2) INFORMATION FOR SEQ ID NO:31:

(i) SEQUENCE CHARACTERISTICS:
      (A) LENGTH: 241 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: TONSNOT01
      (B) CLONE: 735021

(xi) SEQUENCE DESCRIPTION: SEQ ID NO:31:

GCCGACTAGG CGAATTCANT TACTNACCGG NCTGGGCTNC TTTTAGACAT NGAGGAAGNC    60

ANTGAAGGTN GAGGAAATNA TCGTGTNCGG AACCTGCAAA GTNAGGTGGA GGGAGTTAAG    120

AATATTATNA CCCAGAATTT GGAGCGGATN CTNGNCCNGG GGGAAAACTT GGAACATTTN    180

CNNAATNAGN CANAGGGTCT TGAAGNCANA TCTTGCATTT AAGAGGCATG CAAAAGGTTG    240

T    241

(2) INFORMATION FOR SEQ ID NO:32:

(i) SEQUENCE CHARACTERISTICS:
      (A) LENGTH: 231 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: PROSTUT03
      (B) CLONE: 791921

(xi) SEQUENCE DESCRIPTION: SEQ ID NO:32:

CGTGAAGATG ATTGTCCTTA TCTGCGTGAT TGTTTTTATC ATCATCCTCT TCATTGTGCT    60

CTTTGCCACT GGTGCCTTCT CTTAAGTAAC AGGGAACCTC TCCCACCTGC CCTTCTCTTC    120

AGGGACAACC CTCCATAAAT GTGTGCCAAG AGGGTCTCCT TTCCTGTCTT CCTCTACAGA    180

GAATGCTGCT CGGTCCTNCT ACCCCTCTTC CCGAGGCCCT GCTGCCATGT T    231

(2) INFORMATION FOR SEQ ID NO:33:

(i) SEQUENCE CHARACTERISTICS:
      (A) LENGTH: 250 base pairs
      (B) TYPE: nucleic acid
      (C) STRANDEDNESS: single
      (D) TOPOLOGY: linear (ii) MOLECULE TYPE: cDNA (vii) IMMEDIATE SOURCE:
      (A) LIBRARY: PROSTUT03
      (B) CLONE: 791949

(xi) SEQUENCE DESCRIPTION: SEQ ID NO:33:

```
CGTGAAGATG ATTGTCCTTA TCTGCGTGAT TGTTTTTATC ATCATCCTCT TCATTGTGCT      60

CTTTGCCACT GGTGCCTTCT CTTAAGTAAC AGGGAACCTC TNCCACCTGC CCTTCTCTTC     120

AGGGACAACC CTCCATAAAT GTGTGCCAAG AGGGTCTTCT TTCCTGTCTT NCTNTACAGA     180

GAATGCTGCT CGGTCCTCTA CCNCTNTTNC CGAGGCCCTG NTGCCATGTT GTATGCCCCA     240

GAAGGTACCC                                                            250
```

(2) INFORMATION FOR SEQ ID NO:34:

(i) SEQUENCE CHARACTERISTICS:
        (A) LENGTH: 236 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LATRNOT01
        (B) CLONE: 465964

(xi) SEQUENCE DESCRIPTION: SEQ ID NO:34:

```
GGTGACGGAA ATTATGCGTA ACAACTTCGG CAAGGNCCTG GAGCGTGGTG TGAAGCTGNC      60

CGAACTNCAG CAGCGTTCAG ACCAACTACT GGATATGGTA GCTCAACCTT CAACAAGACT     120

ACACAGAACC TNGACCAGAA GAAGTGCTGG GAGAACATNC GTTACCGGAN CTGCGTGGGN     180

CTGGTGGTGG TTGGTGTCNG CTCATNATNC TGATTGTGCT GCTGGTCGTC TTTCTC        236
```

(2) INFORMATION FOR SEQ ID NO:35:

(i) SEQUENCE CHARACTERISTICS:
        (A) LENGTH: 288 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LVENNOT02
        (B) CLONE: 534305

(xi) SEQUENCE DESCRIPTION: SEQ ID NO:35:

```
GGNGAGGNGG NGGNGGCAGC AGCGATGGCA GGAATAGAGT TGGAGCGGTG CCAGNAGCAG      60

GCGAACNGGT GACGGNAATT ATGCGTAACA ACTTCGGCAA GGTNCTGGAG CGTGGTGTGA     120

AGCTNGCCGA ACTNNAGCAG CGTTCAGNCC AACTTTGGAT ATGAGCTNAA CCTTNAACAA     180

GACTACACAG AACCTTGGCC AGAAGAAGTG CTTGGAGGAC ATCCGTTACC GGATCTTTGT     240

GGGGCTNNTG GTGGTTTGTG TCCTGTNAAT ATCCTGATTT GCTGTTGT                 288
```

(2) INFORMATION FOR SEQ ID NO:36:

(i) SEQUENCE CHARACTERISTICS:
        (A) LENGTH: 179 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LVENNOT02
        (B) CLONE: 535203

(xi) SEQUENCE DESCRIPTION: SEQ ID NO:36:

```
CAGGAATAGA GTTGGAGCGG TGCCAGCAGC AGGCGAACGA GGTGACGGAA ATTATGCGTA      60

ACAACTTCGG CAAGGTCCTG GAGCGTGGTG TGAAGCTGGC CGAACTGCAG CAGCGTTCAG     120

ACCAACTNCT GGATATGAGC TNAACCTTCA ACAAGACTAC ACAGAACCTG GGCCAGAAG      179
```

(2) INFORMATION FOR SEQ ID NO:37:

(i) SEQUENCE CHARACTERISTICS:
        (A) LENGTH: 248 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: UTRSNOT02
        (B) CLONE: 679019

(xi) SEQUENCE DESCRIPTION: SEQ ID NO:37:

```
CAGGAATAGA GTTGGAGCGG TGCCAGCAGC AGGCGAACGA GGTGACGGAA ATTATGCGTA      60

ACAANTTCGG CAAGGTCTGG AGCGTTGTTT AAGCTTGNCG AACTGCAGCA GCGTTCAGAC     120

CAACTTCTGG NTATGAGCTC AACCTTTCAA CAAGACTACA CAGAACCTGG CCCAGAAGAA     180

GTGCTGGGAG AACATCCGTT ACCGGATCTG CGTGGGGCTG GTGGTGGTTG GTGTCCTGCT     240

CATCATCC                                                              248
```

(2) INFORMATION FOR SEQ ID NO:38:

(i) SEQUENCE CHARACTERISTICS:
        (A) LENGTH: 227 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT03
        (B) CLONE: 732685

(xi) SEQUENCE DESCRIPTION: SEQ ID NO:38:

```
CAGGAATAGA GTTGGAGCGG TGCCAGCAGC AGGCGAATGA GGTGACGGAA ATTATGCGTA      60

ACAACTTCGG CAAGGTCCTG GAGCGTGGTG TGAAGTTGGC CGAACTGCAG CAGCGTTCAG     120

ACCAACTNCT GGATATGAGC TCAACCTTCA ACAAGACTAC ACAGAACCTG GCCCAGAAGA     180

AGTGCTGGGA GAACATCCGT TACCGNATCT GCGTGGGGCT GGTGGTT                   227
```

(2) INFORMATION FOR SEQ ID NO:39:

(i) SEQUENCE CHARACTERISTICS:
        (A) LENGTH: 191 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: BRAITUT01
        (B) CLONE: 746779

(xi) SEQUENCE DESCRIPTION: SEQ ID NO:39:

```
ATGAGCTCAA CCTTCAACAA GACTACACAG AACCTGGCCC AGAAGAAGTG CTNGGAGAAC      60
```

```
ATCCGTTACC GGATCTGCGT GGGGCTGGTG GTGGTTGGTG TCCTGCTCAT CATCCTGATT    120

GTGCTGCTGG TCGTCTTTCT CCCTCAGAGC AGTGACAGCA GTAGTGCCCC ACGGACCCAG    180

GATGCAGGCA T                                                        191
```

(2) INFORMATION FOR SEQ ID NO:40:

(i) SEQUENCE CHARACTERISTICS:
        (A) LENGTH: 228 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: COLNNOT05
        (B) CLONE: 778289

(xi) SEQUENCE DESCRIPTION: SEQ ID NO:40:

```
CAGGAATAGA GTTGGAGCGG TGCCAGCAGC AGGCGAACGA GGTGACGGAA ATTATGCGTA     60

ACAACTTCGG CAAGGTCCTG GAGCGTGGTG TGAAGCTGGC CGAACTGCAG CAGCGTTCAG    120

ACCAACTCCT GGATATGGTA GCTCAACCTT CAACAAGACT ACACAGAACC TGGCCCAGAA    180

GAAGTGCTGG GAGAACATCC GTTACCGGAT CTGCGTGGGG CTGGTGGT                228
```

(2) INFORMATION FOR SEQ ID NO:41:

(i) SEQUENCE CHARACTERISTICS:
        (A) LENGTH: 210 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: HUVENOB01
        (B) CLONE: 035150

(xi) SEQUENCE DESCRIPTION: SEQ ID NO:41:

```
ATCAGATTTC CAACTTATGC CTTCCAGAAA AAAACACTAC TGCCTAACAC AAATCTGTGA     60

TAACAACAGG CTGTGCCTTA TTTTGATAAT TTNCTGATTC CCTAGAAGAG AACCCNCTAC    120

TTTNTTGTAA GCACTACTGA CTCTCGCTGT ATTTTAAGAT NCTGGTGAAG NGCTNTTTNC    180

TCTTGGCATN AGATTTNAAG ATGTTNTACA                                    210
```

(2) INFORMATION FOR SEQ ID NO:42:

(i) SEQUENCE CHARACTERISTICS:
        (A) LENGTH: 251 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: HUVENOB01
        (B) CLONE: 039462

(xi) SEQUENCE DESCRIPTION: SEQ ID NO:42:

```
CCTGAGTCTG GTATATGCGA TCTCGAGTCG GGTACTTATA CACTGCGGTC ATTTGGNATT     60

ATTNTCAGAN CCACATTNTT AAACCTTTGG GTAATCAGAT TTCCAACTTA TGCCTTCCNG    120

AAAAAAACAC TACTGCCTAA CACAANTCTG NGATANCAAC AGGCTGTGCC TNATTTTGAT    180
```

AATTTTCTGN TNCCCTAGAA GAGAACCCTC TACTTTTTGT AAGCACTACT GACTCTTCGC      240

TNGTATTTAA G                                                          251

(2) INFORMATION FOR SEQ ID NO:43:

(i) SEQUENCE CHARACTERISTICS:
        (A) LENGTH: 260 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: HUVENOB01
        (B) CLONE: 039463

(xi) SEQUENCE DESCRIPTION: SEQ ID NO:43:

TGAGTCTNNT ATATGCGATC TCGAGTCGGG TACTTATACA CTGCGGTCAT TTGGCATTAT       60

TTTCAGAACC ACATTTTAAA CCTTTGGGTA ATCAGATTTC CAACTTATGC CTTCCAGAAA      120

AAAACACTAC TGCCTAACAC AAATCTGTGA TAACAACAGG CTGTGCCTTA TTTTGATAAT      180

NTNCTGATTC CCTAGAAGAG AACCCTCTAC TTTTTGTAAG CACTACTGAC TCTCGCTGTA      240

TTTAAGATGC TGGTGAAAGG                                                 260

(2) INFORMATION FOR SEQ ID NO:44:

(i) SEQUENCE CHARACTERISTICS:
        (A) LENGTH: 203 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT01
        (B) CLONE: 060039

(xi) SEQUENCE DESCRIPTION: SEQ ID NO:44:

CCTCTCNGNNT TTGTAAGCAC TACTGACTCT CGCTGTATTT AAGATGCTGG TGAAGAGCTT      60

TTGCTCTTGC ANTAGATTTG AAGATGTTTA CATTGTTGTT ATTGTTATGT ATCACTTGCT      120

AAAAATATTG TTTTAATCAG AGATAACCTC TTTAAAAAAA TTTTTAAAGA ACTATGGCTA      180

TGACCAAAGC TTCTATTTTG CCG                                             203

(2) INFORMATION FOR SEQ ID NO:45:

(i) SEQUENCE CHARACTERISTICS:
        (A) LENGTH: 205 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT01
        (B) CLONE: 060087

(xi) SEQUENCE DESCRIPTION: SEQ ID NO:45:

GCTTTTNCTC TTGCATTAGA TTTGAAGATG TTTACATTGT TGTTATTGTT ATGTATCACT       60

TGCTAAAAAT ATTGTTTTAA TCAGAGATAA CCTCTTTAAA AAAATTTTTA AGAACTATG      120

GCTATGACCA AAGCTTCTAT TTTNCCAAAA AGTTAAATAC CGNTAAAATG GCCTTAAGTG      180

TATTCCTGNC AGNTAAATTC AGAAT                                             205

(2) INFORMATION FOR SEQ ID NO:46:

(i) SEQUENCE CHARACTERISTICS:
        (A) LENGTH: 230 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: SINTNOT02
        (B) CLONE: 236811

(xi) SEQUENCE DESCRIPTION: SEQ ID NO:46:

AACAGGCTGT GCTTATTTTG ATAATTTCCT GATTCCCTAG AAGAGAACCC TCTACTTTTT       60

GTAAGCACTA CTGACTCTCG CTGTATTTAA GATGCTGGTG AAGAGCTTTT NCNCTTGCAT      120

TAGATTTGAA GATGTTTACA TTGTTGTTAT TGTTATGTAT CACTTGCTAA AAATATTGTT      180

TTAATCAGAG ATAACCTCTT TAAAAAAATT TTTAAAGAAC TATGGCTATG                 230

(2) INFORMATION FOR SEQ ID NO:47:

(i) SEQUENCE CHARACTERISTICS:
        (A) LENGTH: 422 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: RATRNOT01
        (B) CLONE: 354051

(xi) SEQUENCE DESCRIPTION: SEQ ID NO:47:

CTCTTGCATT AGATTTGAAG ATGTTTACAT TGTTGTTATT GTTATGTATC ACTTGCTAAA       60

AATATTGTTT TAATCAGAGA TAACCTCTTT AAAAAAATTT TTAAAGAACT ATGGCTATGA      120

CCAAAGCTTC TATTTTGCCA AAAAGTTAAA TACCGATAAA ATGGCCTTAA GTGTATTCCT      180

GACAGTTAAA TTCAGAAACG TGCCAAATTG GAACTCAAGG TGCCCCTTTC AGAATTAAAT      240

CATTACCTTG TGTGTGAACC TTCTACANCT TCATAGGCCT TCTTCCCTTT GAAAAGGCTG      300

TAGACNTGTN GCTCCCCTCC TGGATTCAGT ATTTGCATGG GGGTTAGAGA AGGTTTAGGT      360

AGCTTTGACC GCTCATAAAG NGTTTTNCCC GCAGTTGGCA GTTATCAGTT GGCTCCAGCA      420

NG                                                                    422

(2) INFORMATION FOR SEQ ID NO:48:

(i) SEQUENCE CHARACTERISTICS:
        (A) LENGTH: 223 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LUNGNOT02
        (B) CLONE: 375070

(xi) SEQUENCE DESCRIPTION: SEQ ID NO:48:

GGTAATCAGA TTTCCAACTT ATGCCTTCCA GAAAAAAACA CTACTGCCTA ACACAAATCT       60

```
GTGATAACAA CAGGCTGTGC CTTATTTTGA TAATTTTCTG ATTCCCTAGA AGAGAACCCT      120

CTACTTTTTG TAAGCACTAC TGACTCTCGC TGTATTTAAG ATGCTGGTGA AGAGCTTTTG      180

CTCTTGCATT AGATTTGAAG ATGTTTACAN NGTTGTTATT GTT                        223

(2) INFORMATION FOR SEQ ID NO:49:

(i) SEQUENCE CHARACTERISTICS:
        (A) LENGTH: 225 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: LATRNOT01
        (B) CLONE: 465647

(xi) SEQUENCE DESCRIPTION: SEQ ID NO:49:

ACAAATCTGT GATAACAACA GGCTGTGCCT TATTTTGATA ATTTTCTGAT TCCCTAGAAG       60

AGAACCCTCT ACTTTTTGTA AGCACTACTG ACTCTCGCTG TATTTAAGAT GCTGGTGAAG      120

AGCTTTTGCT CTTGCATTAG ATTTGAAGAT GTTTACATTG TTGTTATTGT TATGTATCAC      180

TTGCTAAAAA TATTGTTTTA ATCAGAGATA ACCTCTTTAA AAAAA                      225

(2) INFORMATION FOR SEQ ID NO:50:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE:

(xi) SEQUENCE DESCRIPTION: SEQ ID NO:50:

TGTGTTAGGC AGTAGTGTTT TTTTCTGG                                          28

(2) INFORMATION FOR SEQ ID NO:51:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY:
        (B) CLONE:

(xi) SEQUENCE DESCRIPTION: SEQ ID NO:51:

AATCTGTGAT AACAACAGGC TGTGC                                             25
```